United States Patent [19]

Matsumoto et al.

[11] Patent Number: 5,690,895
[45] Date of Patent: Nov. 25, 1997

[54] FLOW CELL APPARATUS

[75] Inventors: Masaetsu Matsumoto, Sendai; Isao Yamazaki, Tsuchiura; Ryo Miyake, Ibaraki-ken; Masaharu Ishii, Ushiku; Ryohei Yabe, Katsuta; Hiroshi Ohki, Tsuchiura; Hideyuki Horiuchi, Abiko; Shinichi Sakuraba, Katsuta, all of Japan

[73] Assignee: Hitachi, Ltd., Tokyo, Japan

[21] Appl. No.: 761,143

[22] Filed: Dec. 6, 1996

Related U.S. Application Data

[63] Continuation of Ser. No. 503,881, Jul. 18, 1995, abandoned, which is a continuation of Ser. No. 186,478, Jan. 26, 1994, abandoned.

[30] Foreign Application Priority Data

Jan. 26, 1993 [JP] Japan ................. 5-010471
May 25, 1993 [JP] Japan ................. 5-122338

[51] Int. Cl.⁶ ........................... G01N 21/05
[52] U.S. Cl. ................. 422/73; 422/81; 356/39; 356/73; 356/246
[58] Field of Search ........................ 356/39, 72, 73, 356/246; 422/63, 67, 68.1, 82.05, 73, 81, 111, 119; 250/461.1, 461.2

[56] References Cited

U.S. PATENT DOCUMENTS

| | | | |
|---|---|---|---|
| 4,338,024 | 7/1982 | Bolz et al. | 356/23 |
| 4,515,274 | 5/1985 | Hollinger et al. | |
| 4,983,038 | 1/1991 | Ohki et al. | |
| 5,007,732 | 4/1991 | Ohki et al. | 356/73 |
| 5,030,002 | 7/1991 | North, Jr. | 356/73 |
| 5,040,890 | 8/1991 | North, Jr. | 356/72 |
| 5,088,816 | 2/1992 | Tomioka et al. | 356/39 |
| 5,138,181 | 8/1992 | Lefevre et al. | 250/573 |
| 5,159,403 | 10/1992 | Kosaka | 356/243 |
| 5,311,290 | 5/1994 | Olson et al. | 356/383 |
| 5,412,466 | 5/1995 | Ogino | 356/246 |

FOREIGN PATENT DOCUMENTS

| | | |
|---|---|---|
| 360487 | 9/1989 | European Pat. Off. |
| 435166 | 12/1990 | European Pat. Off. |
| 478392 | 9/1991 | European Pat. Off. |
| 526131 | 7/1992 | European Pat. Off. |
| 556971 | 2/1993 | European Pat. Off. |
| 564122 | 3/1993 | European Pat. Off. |
| 54-08312 | 4/1979 | Japan |
| 58-26268 | 2/1983 | Japan |
| 64-26125 | 1/1989 | Japan |
| 3105235 | 5/1991 | Japan |

OTHER PUBLICATIONS

Dean, P.N. "Hydrodynamic Orientation of Sperm Heads For Flow Cytometry" Biophysical Journal, vol. 23, pp. 1–13 (1978).

*Primary Examiner*—Jeffrey Snay
*Attorney, Agent, or Firm*—Antonelli, Terry, Stout & Kraus, LLP.

[57] ABSTRACT

A flow cell apparatus, useful in an apparatus for measuring particles suspended in a liquid, comprises a sample liquid supply device, a sheath liquid supply device, a flow cell which has a flow passage passing through a transparent measuring portion, and a nozzle for causing the sample liquid, from the supply device to flow in the flow passage of the flow cell. The nozzle has at least one discharge port which is disposed in the flow passage in a spaced relation from the inner wall of the flow cell flow passage. The sheath liquid supply device causes the sheath liquid to flow around the nozzle discharge port and surround the sample liquid flow to form a sheath flow. The flow passage of the flow cell and the nozzle are so formed as to ensure a sample liquid flow of a fixed width through the measuring portion. A stable sample flow having a fixed width can be formed in the measuring portion even when the flow is at a high velocity, and particles in the sample liquid can efficiently be photographed with high accuracy.

51 Claims, 21 Drawing Sheets

FLOW CELL APPARATUS

This application is a Continuation of application Ser. No. 08/503,881, filed Jul. 18, 1995, now abandoned, which is a continuation of application Ser. No. 08/186,478, filed Jan. 26, 1994 now abandoned.

BACKGROUND OF THE INVENTION

The present invention relates to a flow cell apparatus for obtaining morphological information of particles suspended in a liquid to analyze the information.

A typical example of observing shapes of particles contained in a liquid to classify and analyze the particles is a urine sedimentation examination. The urine sedimentum examination is a morphological examination of particles in urine. Hitherto, employed for the urine sedimentation examination is by a visual method of dyeing sediment to make a specimen on a slide glass plate and inspecting the specimen with a microscope. The sediment contains particles of various sizes from several micrometers, such as blood corpuscle cells and bacilli, to hundreds of micrometers, such as columnar particles. These particles are observed by switching the magnification of the microscope between a high magnification and a low magnification. According to the foregoing method, typically, condensed urine in a quantity corresponding to natural urine of 5 microliters in a case of observation at a high magnification and or in a quantity corresponding to natural urine of 750 microliters in a case of a low magnification is observed to count the number of each sediment component, though the quantity of the sample to be observed varies depending upon the purpose.

There has been another method which utilizes a flow cell having a flow passage of a specific form with a measuring portion provided therein to classify and analyze particles in a liquid. This method is what forms, in the flow passage of a flow cell, a flow of the liquid to be measured, which is surrounded by a sheath flow, and measures particles in the sample liquid by an optical means. Such a method is suitable to automate the examination of particles in a liquid. For example, National Publication of Unexamined Application No. 57-500995 has disclosed an apparatus in which a fluid sample is introduced into a flow passage of a specific shape and particles in the sample are photographed in a wide imaging region. The apparatus has a CCD camera connected to a microscope and a pulse light source for periodically emitting light in synchronization with the operation of the CCD camera, so that enlarged still images of particles even flowing can be taken with the CCD camera. Through analysis of the still images thus obtained, the particles in a liquid can morphologically be analyzed. Further, the concentration of the particles may be analyzed by counting how many the particles are contained in a volume of the photographed sample.

Another method using a flow cell has been suggested, in which condition of a sample flow are varied during measurement of the same kind sample to change the state of the sample flow to measure the same. According to this method, the sample can be measured under a plurality of different conditions. An apparatus has been disclosed, as an example of such measurement, in Japanese Patent Unexamined Publication No. 3-105235. The apparatus is what utilizes the flow cell capable of forming a flat sample flow to measure particle components in urine.

The above flow cell is so formed that a flow passage in a measuring portion is constant in size in the direction of thickness of a sample flow while gradually widening in the widthwise direction toward the downstream. The sample flow is widened in the widthwise direction thereof when it passes through the enlarged flow passage, to be decelerated and form a flat flow. The flow thus formed is thin in the direction of thickness of the flow while being wide in the widthwise direction thereof, and particles contained in a part of the flat sample flow are photographed. In the measurement described in Japanese Patent Unexamined Publication No. 3-105235, a microscope is switched between a high magnification mode and a low magnification mode to measure particles of various sizes. At this time, by changing the flow rate of the sample liquid or the sheath liquid to be supplied to the flow cell, the thickness of the sample flow can be controlled. That is, since the depth of focus of the microscope decreases when the sample flow is measured at a high magnification, the thickness of the sample flow is reduced so that the microscope can be focused on particles. In the case of a low magnification, the control is made contrarily.

When using such an apparatus as disclosed in National Publication No. 57-500995 in an examination for a liquid having a low concentration of particles, such as an examination of urine sedimentation, the sample must be subjected to centrifugation. This is because that the concentration of the particles is too low and, unless centrifugation of the sample, most of the images taken will be wasteful with no images of particles photographed therein. For instance, particles contained in urine are usually one or less per microliter and, without condensation of urine, there will be a case where no particle is photographed in 100 visual fields even at a low magnification.

Accordingly, in order to accurately analyze a sample of a low concentration that contains only few particles to be analyzed, the volume of the sample to be analyzed must be increased to increase the number of particles to be measured. To efficiently perform such measurement, therefore, it is desirable to increase the velocity of the sample flowing in the flow cell.

However, in the enlarged flow passage disclosed in National Publication No. 57-500995 which becomes wider in the measuring portion when the velocity is increased, there is a fear that the sample flow will fall into turbulence not to be uniform in thickness and to be uneven in the velocity distribution. This is disadvantageous when photographing particles with accuracy in the visual field of the measuring portion. Further, the sample flowing through the flow passage becomes a flat flow having an elliptic cross sectional shape, and the volume of the sample in the visual field of the measuring can hardly be stable. When a part of the sample flow is photographed for measurement, there will be a case where some particles pass out of the visual field for the measurement and accurate information of the particles and that of the concentration of the sample cannot be obtained.

As described above, according to the conventional method as disclosed in National Publication No. 57-500995, the volume of a sample that can be analyzed within a given period of time is very small, and therefore, it is difficult to accurately obtain many images of particles in a low concentration sample within a given period of time.

Moreover, in order to measure a sample under various conditions, it is desirable to arbitrarily control the shape of a sample flow. In the apparatus disclosed in Japanese Patent Unexamined Publication No. 3-105235, a sample liquid of a circular cross section discharged through a columnar nozzle is once squeezed and then laterally widens to be flat while decreasing its velocity in the enlarged flow passage. In this case, since only the flow rate of the sample liquid and that of the sheath liquid are parameters for controlling the state of the sample flow, it is difficult to individually and arbitrarily control the flow velocity of a central portion of the sample flow and the thickness of the sample flow.

On the other hand, in the above apparatus, when the flow rate of the sample liquid and that of the sheath liquid are set to cause the flow velocity of the central portion of the sample flow and the thickness thereof to be desired values, the width of the sample flow and the flow velocity of peripheral portions thereof cannot be controlled. That is, the width of the sample flow and the flow velocity of the peripheral portions of the sample flow depend on the shape of the fluid passage, and they cannot be controlled.

In the apparatus disclosed in Japanese Patent Unexamined Publication No. 3-105235, the sample flow is laterally widened in the enlarged, decelerating flow passage to be a flow which is wider than a range required to measure the sample flow, and a part of the sample flow is photographed. As a result, there will be a case where the particle image becomes broken at an end of the photographed image. Further, the flow velocity becomes uneven between the central portion and the peripheral portion of the sample flow.

As described above, according to the conventional method disclosed in Japanese Patent Unexamined Publication No. 3-105235, it is difficult to individually, actively and arbitrarily control the shape and the flow velocity of the sample flow in the flow cell.

SUMMARY OF THE INVENTION

The present invention has a primary object of providing a flow cell apparatus which can accurately and efficiently obtain many particle images even when a liquid to be measured has a low concentration of particles suspended therein.

Another object of the invention is to provide a flow cell apparatus capable of forming a stable, flat and high speed sample flow which is less in turbulence.

Still another object of the invention is to provide a flow cell apparatus which can change the width of a sample flow.

Still another object of the invention is to provide a flow cell apparatus which can change the shape of a sample flow.

Still another object of the invention is to provide a flow cell apparatus, essential portions of which can easily be cleaned in a short time and the maintenance of which is easy to be made.

Still another object of the invention is to provide a flow cell apparatus which can independently control the width, the thickness and the flow velocity of a sample flow to cause the sample flow to pass within a measuring range and in order to make the flow velocity at the central portion and that at the peripheral portion to be uniform.

To attain the foregoing objects, the invention is first intended to form, in a measuring portion, a sample flow of a fixed width which is less in turbulence and hard to cause unevenness in flow velocity between the central portion and the peripheral portion. If the flow is stable even at high velocity, the sample liquid can accurately and efficiently be measured.

According to the invention, a flow cell apparatus for measuring particles suspended in a liquid comprises means for supplying a sample liquid to be measured, means for supplying a sheath liquid, flow cell means for defining a flow passage. The flow cell means having a transparent measuring portion for providing an unobstructed view of the flow passage in at least one transversal direction thereof, and nozzle means provided in fluid communication with the sample liquid supply means for causing the sample liquid to flow into the flow passage of the flow cell means. The nozzle means has at least one discharge port which is disposed in the flow passage in a spaced relation from an inner wall of the flow passage. The sheath liquid supply means is in fluid communication with the flow passage of the flow cell means at a position upstream the discharge port of the nozzle means with respect to the flow of the sample liquid to cause the sheath liquid to flow around the discharge port and surround the sample liquid flow from the discharge port to form a sheath flow. The apparatus further comprises means for making the sample liquid flow have a substantially constant width in at least a direction perpendicular to a direction of the unobstructed view in the measuring portion.

It is preferable that the flow cell means further includes means provided upstream the measuring portion for narrowing the sheath flow in the unobstructed view direction of the measuring portion to increase a velocity of the sample liquid flow in the sheath flow and reduce a thickness of the sample liquid flow in the unobstructed view direction to form a flat flow.

It is preferable that the nozzle means further includes means for changing the width of the sample liquid flow in accordance with a measuring range in the measuring portion.

Moreover, it is preferable that the nozzle means further includes means for changing the shape of the sample liquid flow.

Preferably, the substantially constant width sample liquid flow making means may further include guide means disposed on opposite sides of the discharge port in the widthwise direction of the flow passage for guiding the sample liquid from the discharge port to form a stable flow of the constant width.

DESCRIPTION OF THE DRAWINGS

All drawings accompanied illustrate embodiments and modifications of the present invention, wherein.

DESCRIPTION OF THE EMBODIMENTS

The basic structure of a flow cell apparatus according to the invention will now be described with reference to an embodiment shown in FIGS. 1 to 9. The flow cell apparatus shown in these figures exhibits the basic characteristic features of the invention and some additional features. The flow cell apparatus comprises a flow cell assembly and a means for supplying a sample.

Figure 1:
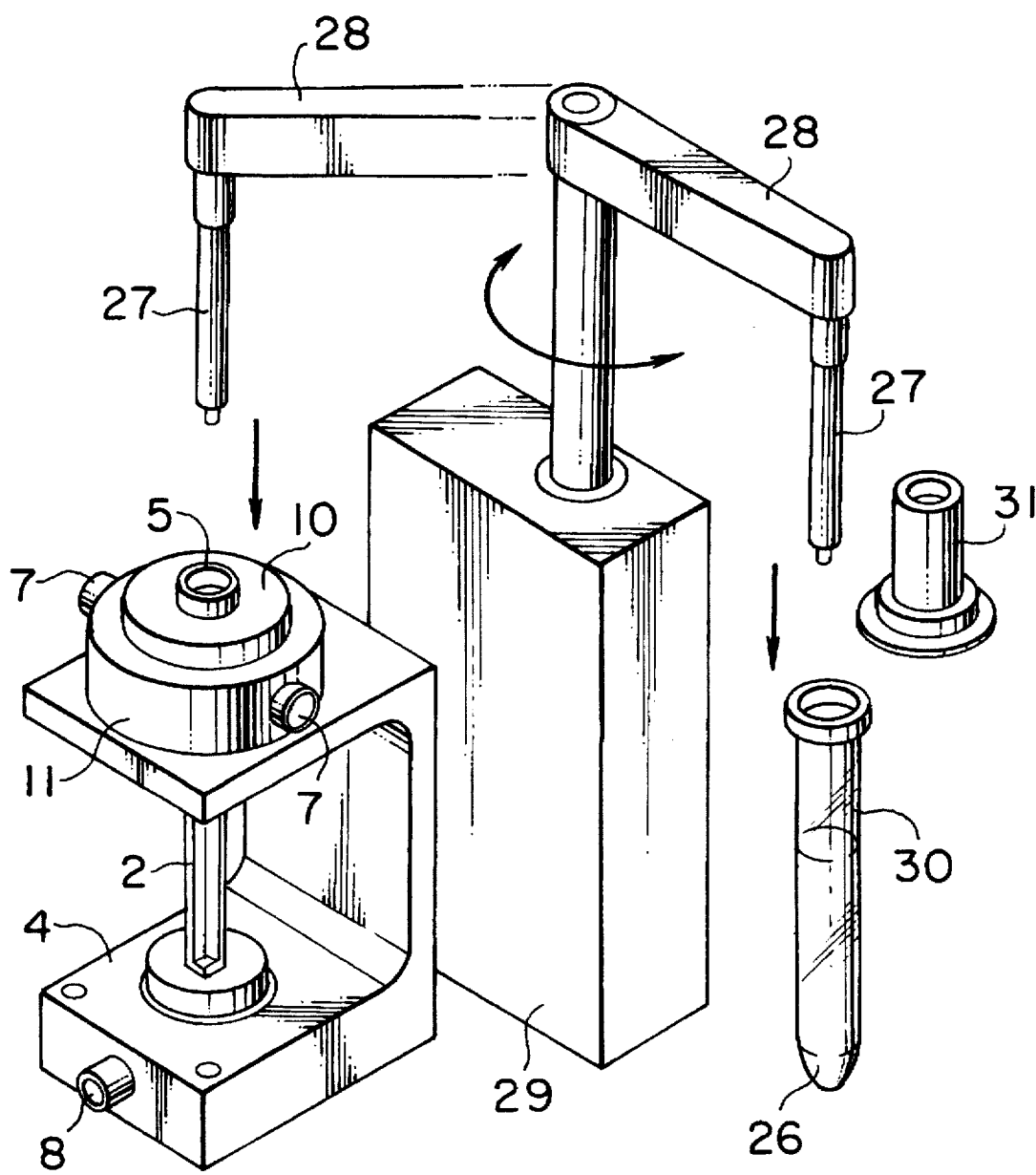
FIG. 1 is a perspective view showing the overall structure of a flow cell apparatus according to a first embodiment of the invention.
Figure 2:
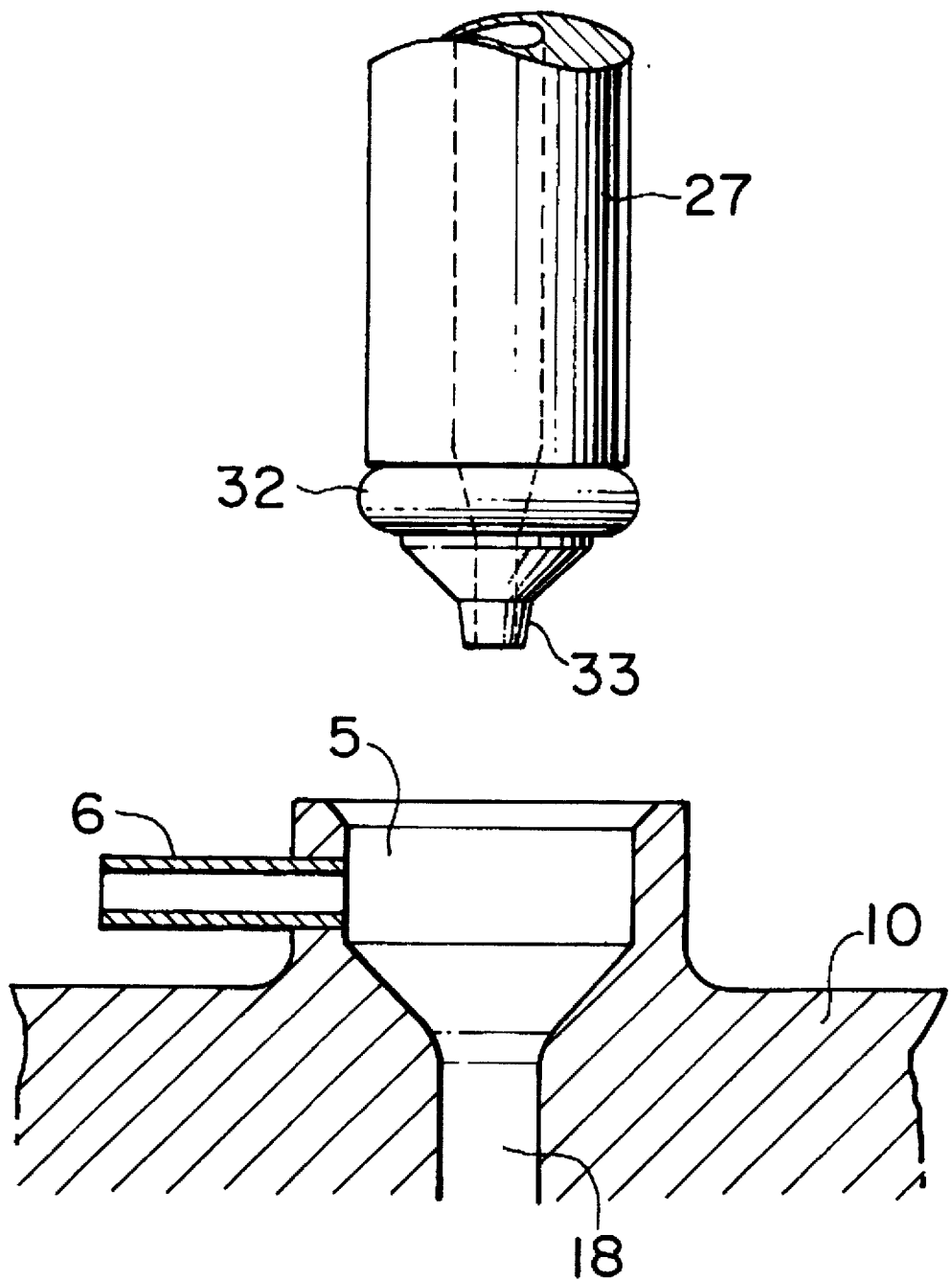
FIG. 2 is an enlarged view for explanation of the connection between a flow cell and a sample fluid supply portion in the apparatus shown in FIG. 1.

As shown in FIG. 1, the means for supplying a sample to a flow cell, which will be described later, is mainly composed of a pipette drive unit 29, a pipette arm 28 which is moved vertically and rotated by the pipette drive unit 29, and a pipe-shaped pipette 27 which is provided at a free end of the arm 28 to extract and supply a sample 26. As shown in FIG. 2, an O-ring 32 is attached to an end of the pipette 27 to improve the air tightness with a connection portion 5 of the flow cell. A sample suction port 33 in an end of the pipette 27 is tapered in order to prevent falling of the sample.

Accordingly, the end of the pipette 27 and the connection portion 5 can be joined in intimate contact to each other to prevent leakage of the sample 26.

In this embodiment, the sample supply means is constructed as described above. Therefore, a sample can continuously and quickly be supplied to the flow cell serving as a measuring section, and the embodiment has an advantage of being able to adapt to a case where many kinds of samples are successively measured.

Further, the sample is not required to be introduced into the measuring section through a tube or the like, and accordingly it can directly be supplied from a position adjacent to the measuring section. Therefore, time taken to form a sheath flow in the flow cell can significantly be shortened. In the case where a sample is transported for a relatively long distance to the measuring section through a tube or the like, the overall passage, through which the sample has passed, must be cleaned. However, this embodiment, because of having the very short sample passage as described above, enables the area, that must be cleaned, to considerably be reduced. Further, cleaning can be performed by directly inserting the end of the pipette 27 into a cleaning tank 31, so that time required to complete the cleaning can be shortened.

Figure 3:
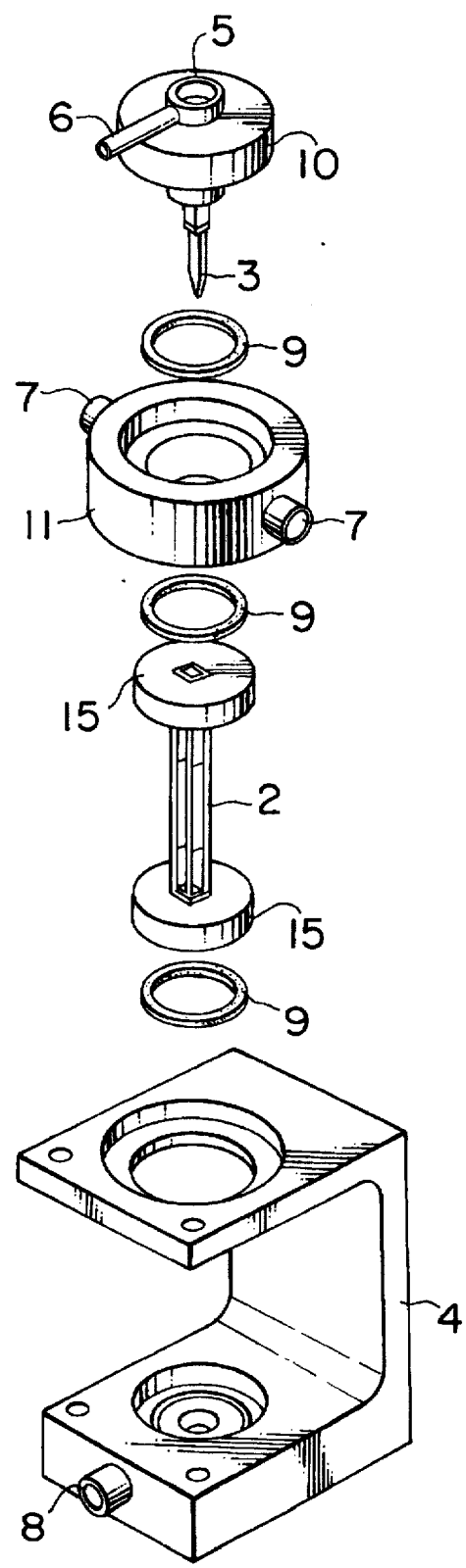
FIG. 3 is an exploded perspective view showing an essential structure of the flow cell shown in FIG. 1.

The flow cell assembly according to this example is constituted as follows. As shown in FIG. 3, a holder 4 has a seat formed on the bottom thereof. One of flanges 15 for holding a casing 2 which defines a flow passage is joined into intimate contact to the seat while being sealed with an O-ring 9. The other flange 15 is joined into intimate contact to a sheath liquid supply portion 11 while being sealed with an O-ring 9, and the sheath liquid supply portion 11 is installed to the holder 4. The sheath liquid supply portion 11 is provided, in the outer periphery thereof, with sheath liquid ports 7 for supplying a sheath liquid, and these ports are connected to a passage formed through the center of the supply portion 11. The central passage of the supply portion 11 communicates with the flow passage of the casing 2. A sample supply portion 10 is attached in intimate contact to the sheath liquid supply portion 11 while being sealed by another O-ring 9. The sample supply portion 10 is provided with a nozzle 3 serving as an outlet of the sample and the connection portion 5 through which the sample is supplied into a fluid passage for the nozzle 3. The connection portion 5 has a cleaning fluid suction port 6 provided for sucking waste fluid that has cleaned the flow cell. Also in the holder 4, a waste fluid port 8 for discharging waste fluid is formed. The nozzle 3 of the supply portion 10 is inserted into the flow passage of the casing 2 through the central passage of the supply portion 11.

Figure 4:
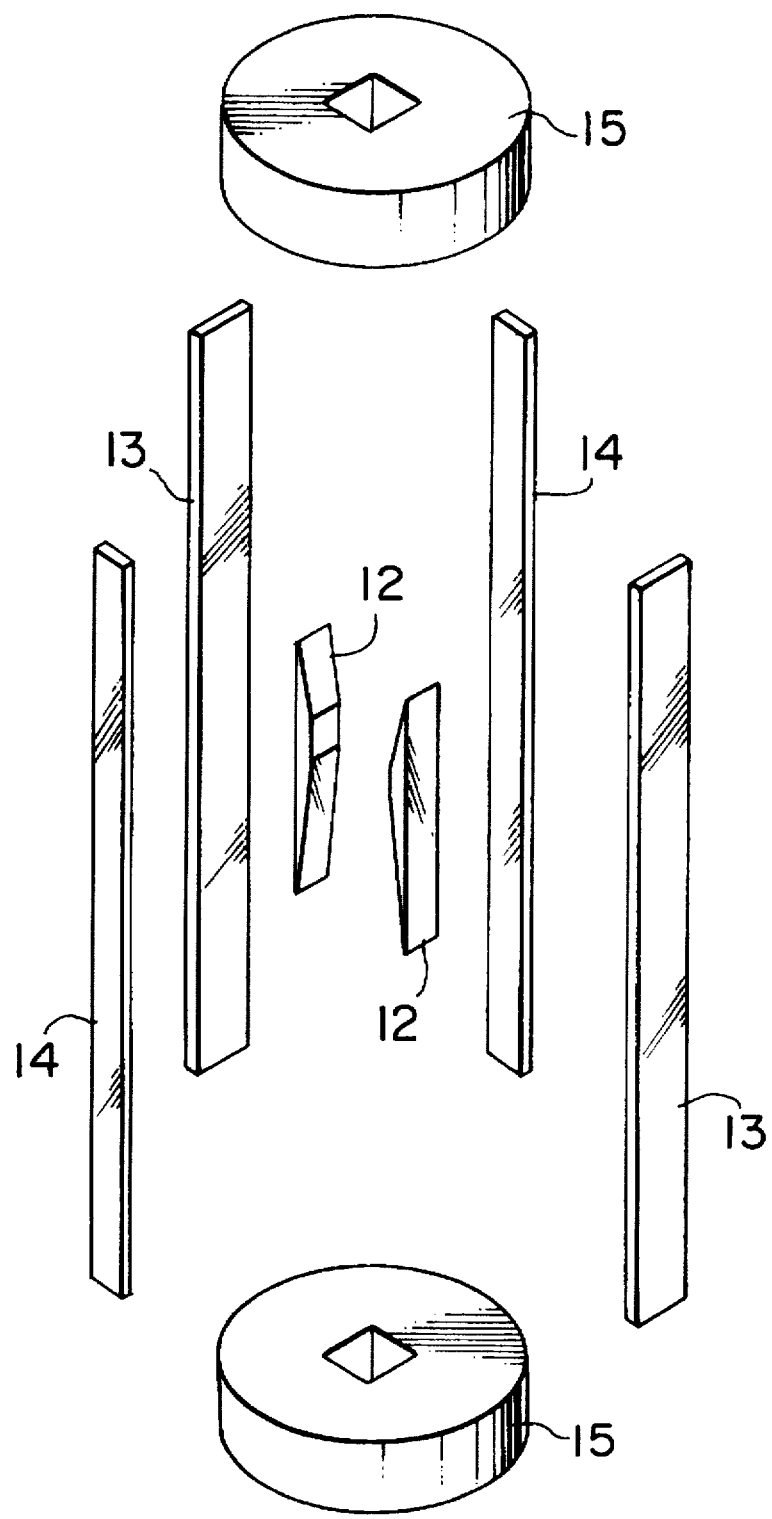
FIG. 4 is an exploded perspective view of a casing in the flow cell of FIG. 3.

The casing 2, as shown in FIG. 4, comprises front plates 13, side plates 14 and flow contraction plates 12, all of which are made of a transparent material so that a flow of the sample in the flow passage is optically measured from outside. The flow passage in the casing 2 is defined by the elongated and flat front plates 13 and the side plates 14 with respective two plates of the same kind combined to each face the associated plate in such a manner that the width and the thickness of the flow passage are made constant. The flow contraction plate 12, which are in a trapezoidal shape thickened substantially at its lengthwise middle portion, are attached in the flow passage to face each other, so that the flow passage is partially narrowed in the direction of the thickness thereof. The front plates 13, the side plates 14 and the flow contraction plates 12 are made of, for example, glass, and assembled by optical bonding without deteriorating their transparency. The front plates 13, the side plates 14 and the contraction flow plates 12 are further secured by means of the flanges 15 at the upper and lower ends of the flow passage.

Figure 5:
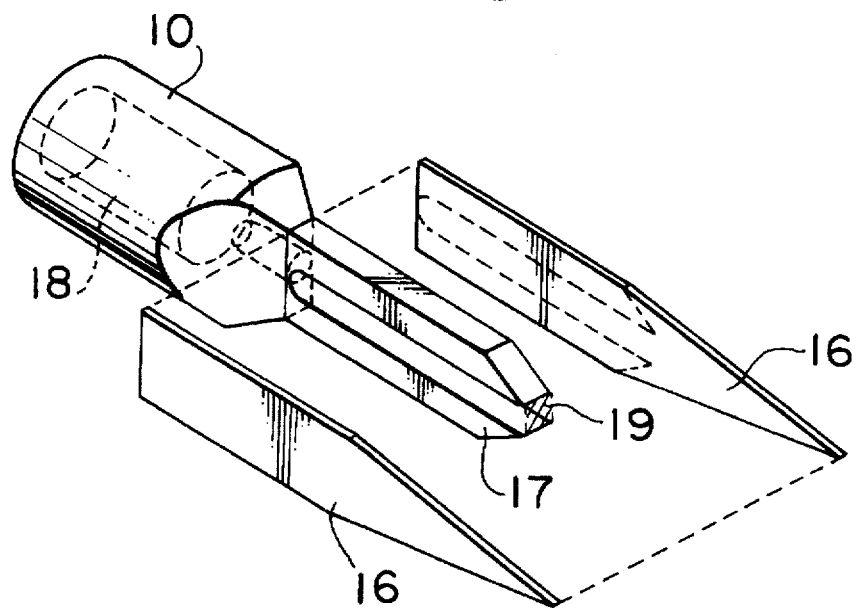
FIG. 5 is an exploded perspective view of a nozzle in the flow cell of FIG. 3.

As shown in FIG. 5, the nozzle 3 comprises a nozzle body 17 with two guides 16 joined respectively on the both sides of the nozzle body, which are longer than the nozzle body and each have a tapered end. The nozzle body 17 is directly fixed to the sample supply portion 10, a sample discharge port 19 of a substantially square cross in the nozzle body is in communication with the connection portion 5 through the sample passage 18, and the sample liquid injected through the connection portion 5 is discharged from the sample discharge port 19. The nozzle body 17 is machined and manufactured from a stainless material by, for example, a wire discharge process. The guide 16 are joined with high accuracy by, for example, a plating joining process.

With the flow cell assembly thus formed, in which the casing 2 is attached to the holder 4 and the sample supply portion 10 with the nozzle 3 is attached to the sheath liquid supply portion 11 which is fixed to the holder 4, the embodiment has an advantage that adjustment, such as position aligning of the nozzle 3 and the casing 2, can be easily performed. Further, disassembling and cleaning of the casing 2 and the sheath liquid supply portion 11, that are considered to be contaminated most frequently, are facilitated, making the maintenance easy.

Supply of a sample to the flow cell 1 (see FIG. 6) is carried out as follows by the foregoing sample supply means. First, the pipette arm 28 is moved vertically and rotated by the pipette drive unit 29 so that the pipette 27 is inserted into a sample container 30 in which the sample 26 is stored. Then, a syringe (not shown in the figures) connected to the pipette 27 is operated to suck the sample 26 of a predetermined quantity into the pipette 27. After that, the pipette 27 is lifted and rotated to be moved to the position above the connection portion 5. The end of the pipette 27 and the connection portion 5 are brought into intimate contact to be connected to each other, then, the syringe is operated to discharge the sample 26 of a certain quantity from the connection portion 5 into the flow cell 1 at a regular rate, and the sample 26 is measured in the flow cell 1. At this time, as the connection portion 5 is directly connected to the sample passage 18, the sample 26 discharged from the pipette 27 passes through the sample passage 18 to be supplied into the flow cell 1 from the nozzle 3. Simultaneously, the sheath liquid is supplied to the ports 7 of the sheath liquid supply portion 11 and flows into the flow cell 1 through the central passage of the supply portion 11 to surround the nozzle 3.

Figure 6:
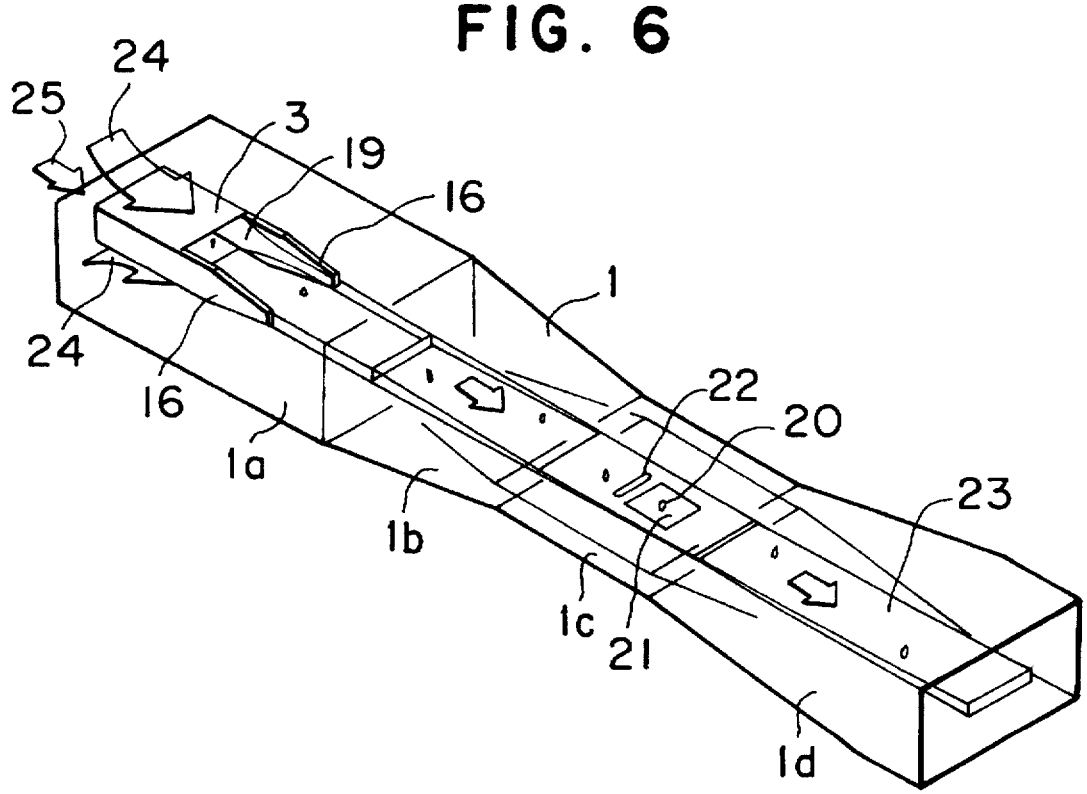
FIG. 6 is a perspective view showing a flow in the flow cell of FIG. 3.

The flow passage in the flow cell 1 is formed as shown in FIG. 6 to have a parallel flow passage portion 1a, a flow contraction passage portion 1b, a flow passage portion 1c for measurement including an imaging portion 21, and a flow rate decelerating passage portion 1d. The sample liquid containing particles 20 to be examined is supplied in a flowing direction 25 and discharged into the flow passage from the nozzle 3 in a predetermined quantity. On the other hand, the sheath liquid which is a clean liquid containing no particles is supplied in a flowing direction 24 into the flow passage around the nozzle 3. A sheath flow, that is a steady laminar flow in which the sheath liquid surrounds the sample liquid, is formed in the flow cell 1, and a sample flow 23 passes through the parallel flow passage portion 1a of the flow cell 1 at a constant speed. The sample flow 23 in the sheath flow flows while having a thin, wide and flat cross section due to pressure applied from the upper and lower sheath flows.

The flow cell passage of the embodiment is formed in a shape, which is monotonously decreased in cross sectional area only in the direction of the thickness thereof from the sample discharge port 19 to the imaging portion 21 due to the provision of the flow contraction plates 12 described above, and it has the flow contraction passage portion 1b. In this flow contraction passage portion, the sheath flow monotonously increases its flowing speed. With this flow speed increasing passage portion, it is possible to form a stable flow, and therefore, a sample flow at a high speed more than 1000 mm/second can be formed. Further, since the sample flow 23 is able to stably flow and wakes in the directions of the thickness and the width are reduced, an improvement in the imaging accuracy can be realized. Moreover, the sample flow discharged from the nozzle 3 is uniformly contracted or reduced in size in the direction of the thickness thereof to form a thinner and uniform flat flow, and therefore, a further improvement in the imaging accuracy can be realized.

The measurement passage portion 1c follows the foregoing passage portion 1b, in which the thickness of the fluid passage is made substantially constant. The sample flow 23 is formed into a flat shape, the cross section of which has a very large aspect ratio such that the width of the sample flow 23 is about 200 to 300 micrometers and the thickness is about 5 to 20 micrometers. The flow passage in the imaging portion 21 is formed in a cross sectional shape which is sufficiently large in size in the widthwise direction as compared with its size in the direction of the thickness thereof, and the width of the flow passage is not changed from the outlet port of the nozzle to the measuring portion. Therefore, the sample flow 23 can be realized to be substantially constant in width and uniform in the flow rate distribution in the direction of the width thereof. The sheath flow then passes through the flow decelerating passage portion 1d and is discharged from the waste fluid port 8 of the holder 4.

The particles 20 to be examined, which are contained in the sample flow 23, are photographed in an imaging visual field 21 by, for instance, a CCD camera connected to a microscope, so that they can be received as image information. The sample flow 23 is in the shape which is small in thickness and large in width. Such a flat shape is suitable easy to be focused on in the range of the imaging visual field 21 when the particles 20 to be examined are imaged by the CCD camera connected to the microscope, and therefore, it is suitable for photographing. For this reason, even in case of a microscope which is shallow in depth of focus, the particles 20 can be imaged in a condition of being correctly focused thereon.

The nozzle 3 is provided with guides 16 which prevent turbulence of the flow of the sample liquid at the sample discharge port 19 and serve to keep the sample flow having a constant width. That is, the width of the sample flow 23 depends on the distance between the two guides 16 of the nozzle 3, and is kept substantially constant from the nozzle 3 to the imaging portion 21 because the width of the flow passage is made constant. Thus, through adjustment of the distance between the guides 16, the sample flow 23 can be set at a suitable width which is optimum for the imaging portion 21.

After the measurement has been completed, the end of the pipette 27 is moved away from the connection portion 5 and is then inserted into a cleaning tank 31. In the cleaning tank 31, a cleaning liquid is radially applied to the end of the pipette 27 to wash out the sample on the pipette 27. Further, a cleaning liquid is supplied also from the inside of the pipette 27 and discharged, together with the sample removed from the interior, into the cleaning tank 31. Since the pressure in the sample liquid passage 18 is somewhat higher than that of the outside air when the end of the pipette 27 is separated from the connection portion 5, the sheath liquid is caused to rise through the sample liquid passage 18 to the connection portion 5 in a state where the pipette 27 is disconnected after the measurement has been completed. The connection portion 5 has the waste liquid suction port 6 (see FIG. 2) provided for sucking the sheath liquid that has cleaned the connection portion 5, and the sheath liquid is sucked through the waste liquid suction port 6, so that the sample adhered to the connection portion 5 is cleaned by the sheath liquid thus sucked.

Figure 7:
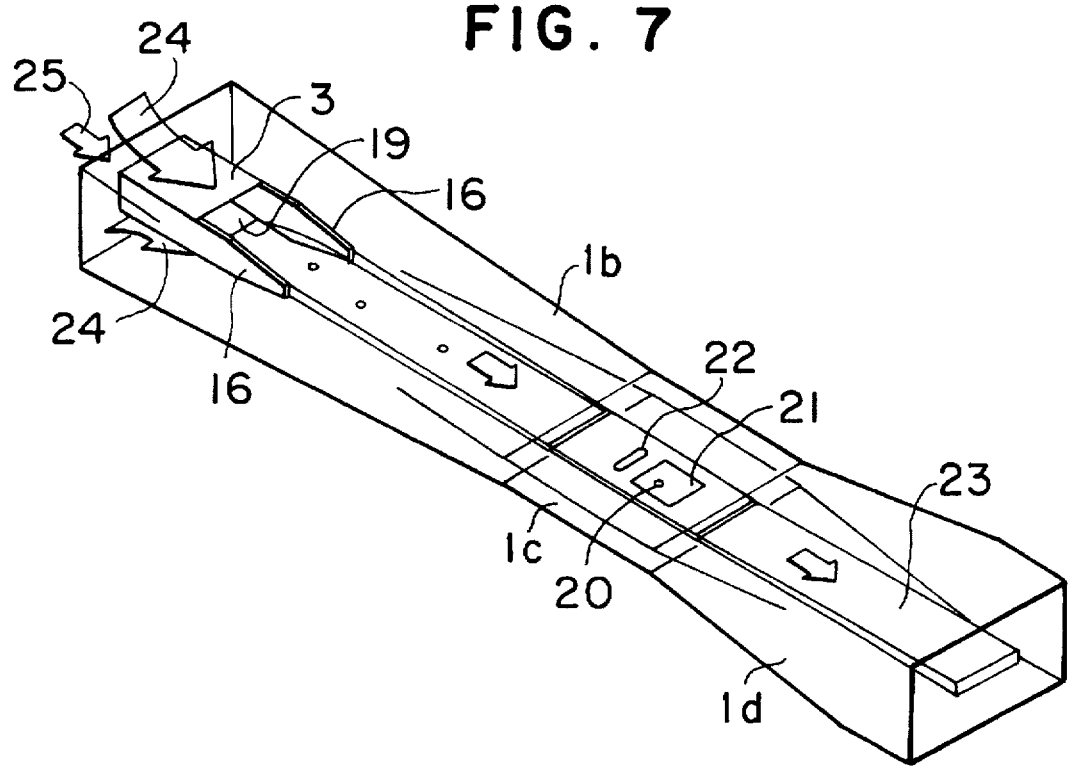
FIG. 7 is a perspective view showing a flow in a flow cell according to a modification.

The flow cell 1 shown in FIG. 6 forms the parallel flow passage portion 1a. As shown in FIG. 7, however, another structure may be employed in which the parallel flow passage portion 1a is omitted from the flow cell 1, the other structural portions are the same as those shown in FIG. 6, and the nozzle 3 is disposed in the flow contraction passage portion 1b. With such a structure, reduction or contraction of a flow is carried out in the flow contraction passage portion 1b at the same time when shaping of the flow is made between the guides 16, so that the sample flow is efficiently formed. Incidentally, in the embodiments and modifications described herein, similar component parts will be denoted by the same reference numerals, and description thereof will be omitted.

Figure 8:
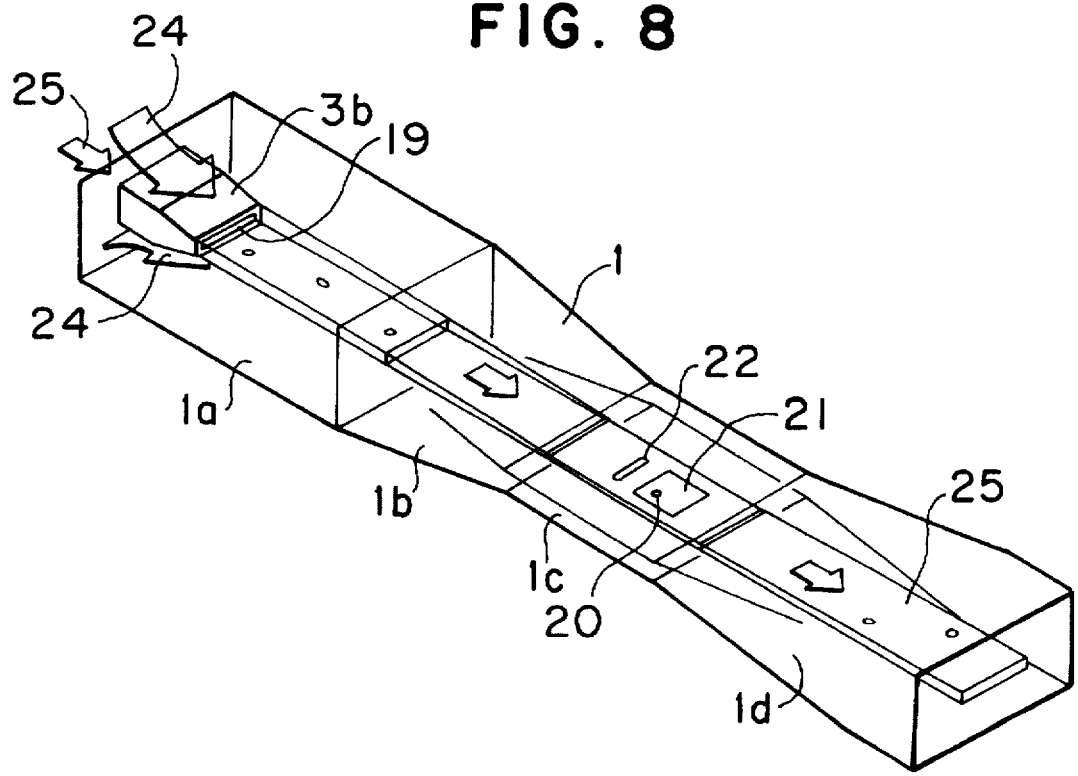
FIG. 8 is a perspective view showing a flow in a flow cell according to another modification.

Further, as shown in FIG. 8, though a similar structure to that of the flow cell 1 shown in FIG. 6 is employed, the guides 16 may be omitted from the nozzle 3. In this modification, the sample discharge port 19 has a wide cross sectional shape, and a wide flow is formed just at the outlet port of the nozzle 3.

Figure 9:
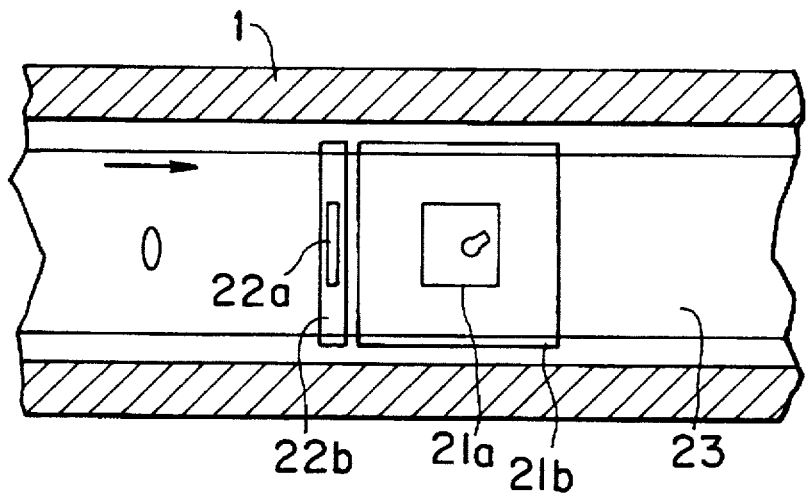
FIG. 9 is an enlarged plan view showing a measuring portion in the flow cell of FIG. 6.

The width of the sample flow 23 and the imaging region 21 will now be described in detail with reference to FIG. 9. The flow cell according to the embodiment shown in FIG. 6 is adapted to detect, by means of an optical system (not illustrated) whether or not the sample particles have passed through the upstream of the imaging portion 21 of the flow cell. That is, the structure is so constructed that a region indicated by reference numeral 22 is irradiated with, for example, laser beams, and dispersed light from the sample particles is detected. The particles contained in the sample liquid are irradiated with the laser beams when they pass through a particle detection region 22a or 22b so that passing of the particles is detected. The particles thus detected are photographed and recorded by an imaging region 21a or 21b.

The flow cell according to this embodiment is so formed that the magnification of photographing the sample particles can be selected from a plurality of magnifications. Therefore, particles contained in the sample and having various sizes, such as large particles of about 100 microns to small particles of several microns, can accurately be photographed. For example, in a mode of photographing particles at a large magnification, they are detected in the particle detection region 22a, and their images are photographed in the enlarged visual field 21a. In another mode in which the particles are photographed at a relatively reduced magnification, they are detected in the particle detection region 22b, and their images of the particles are photographed in the visual field 21b which is not enlarged.

Figure 10A:
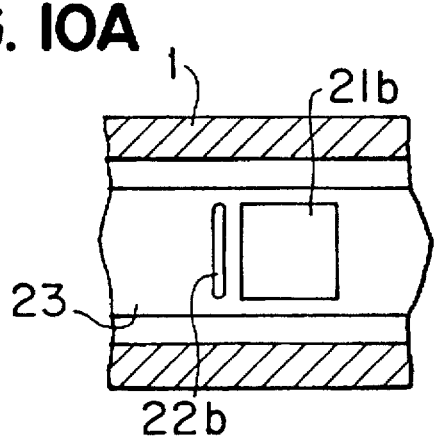
FIGS. 10A to 10H are enlarged plan views illustrating methods of changing an imaging visual field in the flow cell and the way of causing the sample fluid to flow, respectively.
Figure 10B:
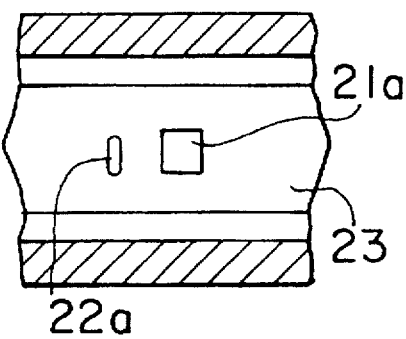
Figure 10C:
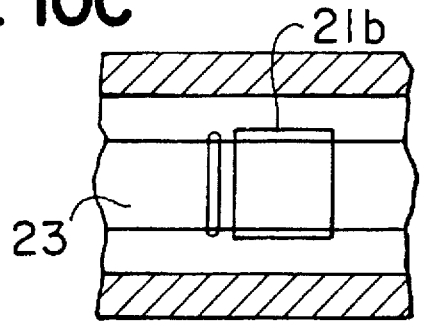

The relationship between the photographing visual field and the width of the sample flow will be described in detailed with reference to FIGS. 10A to 10D. FIGS. 10A to 10C respectively illustrate some methods of changing the photographing visual field and the way of letting the sample fluid to flow. In each method, the detection region 22, the photographing region 21 and/or the sample flow 23 are switched between the low magnification mode and the high magnification mode.

According to the method shown in FIG. 10A, the width of the sample flow 23 is not changed between the low magnification mode and the high magnification mode, but the flow rate and the thickness of the sample are switched. The width of the sample flow 23 is set to be larger than the width of the photographing region 21 in either mode. The width of the detection region 22 is changed to substantially coincide with the width of the photographing region 21.

In this method, only a part of the sample flow discharged in the flow cell 1 passes through the photographing region 21. By having investigated the proportion of the sample flow that passes through the photographing region 21, the volume of the sample liquid that is passing through the photographing region can accurately be known. Further, as the width of the detection region 22 is changed to the same as that of the photographing region 21 at the time when switching the mode, the particles detected in the detection region 22 always pass through the photographing region 21. Only the flow rate and the thickness of the sample flow are controlled, and the width of the same is not required to accurately coincide with the photographing region. Since only the central portion of the sample flow 23 is measured, the flow is required only to have a constant speed and a constant thickness, and the structure of the flow cell 1 can be simplified. Further, since the sample flow 23 passes uniformly over the entire width of the photographing region 21 in either mode, the area of the photographing region 21 can effectively be used, and the efficiency of the analysis can be improved. Moreover, as the sample flow 23 is large in width, the flow passage can be enlarged and hardly clogged even when large particles are contained in the sample flow 23. Also in the method shown in FIG. b, the width of the sample flow 23 is not changed between the low magnification mode and the high magnification mode, but the flow rate and the thickness are switched. The width of the sample flow 23 is made to be slightly narrower than that of the photographing region 21b employed in the low magnification mode, through setting of the dimensions of the discharge port 19 and the guides 16 of the nozzle. The width of the detection region 22 is changed to substantially coincide with the width of the photographing region 21.

In the this method, only a part of the sample liquid discharged in the flow cell 1 passes through the photographing region 21a in the high magnification mode. By having investigated the proportion of the sample liquid that passes through the photographing region 21a, the volume of the sample that passes through the photographing region can accurately be known. Since the photographing region 21a and the detection region 22a have substantially the same width, the particles detected in the detection region 22a always pass through the photographing region 21a. Further in the low magnification mode, as all the sample liquid discharged in the flow cell 1 passes through the photographing region 21b, the volume of the sample liquid passing through the photographing region can be known more accurately. In the high magnification mode in which the depth of focus of the microscope is shallow, only the central portion of the sample flow 23, that flows at a constant speed and has a uniform thickness, is measured. Therefore, image blur occurring due to unevenness of the thickness can be prevented, and analysis of even particles having very small sizes can precisely be performed. Moreover, since only the flow rate and the thickness of the sample liquid flow are controlled, the necessity of accurately regulating the width can be eliminated, and the structure of the flow cell 1 can be simplified. Further, the sample flow 23 uniformly passes substantially over the entire width of the photographing region 21 in either mode, accordingly, the area of the photographing region 21 can effectively be used, and the analysis can be made efficiently.

Also in the method shown in FIG. 10C, the width of the sample flow 23 is not changed between the low magnification mode and the high magnification mode, but the flow rate and the thickness are switched. The width of the sample flow 23 is made slightly narrower than the width of the photographing region 21a employed in the high magnification mode. The width of the detection region 22 is not changed even when the mode is changed.

In this method, in either mode, all the sample liquid discharged in the flow cell 1 passes through the photographing region 21, and therefore, the volume of the sample liquid passing through the photographing region can accurately be known. Further, the width of the detection region 22 is not required to be changed, so that the optical system for detection can be simplified, the apparatus can be reduced in size and the adjustment procedure can be simplified. Since only the flow rate and the thickness of the flow of the sample liquid are controlled, the necessity of accurately regulating the width can be eliminated, and the structure of the flow cell 1 can be simplified. Further, as the sample flow 23 uniformly passes through substantially the overall all width of the photographing region 21b in the high magnification mode, the area of the photographing region 21 can effectively be used, and the analysis can efficiently be performed. Since the width of the sample flow 23 is kept narrow also in the low magnification mode, the sample flow 23 can stably flow even at a high speed, and the analysis can efficiently be performed. Moreover, because the particles do not pass through the ends of the photographing region 21b, the overall shapes of the particles can be photographed, and the image analysis can accurately be performed.

Figure 10D:
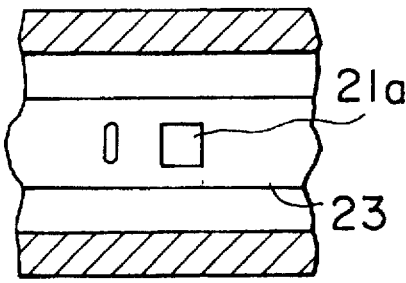
Figure 10E:
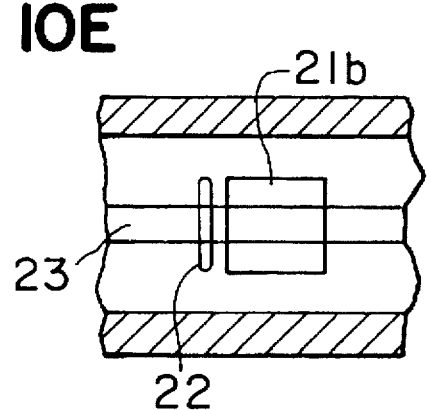
Figure 10F:
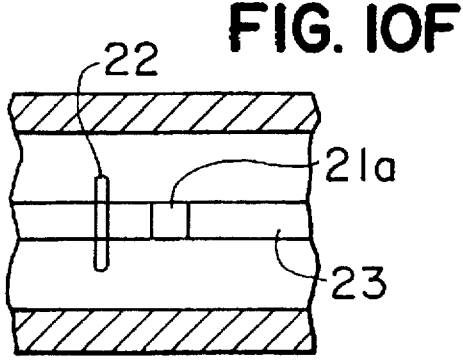
Figure 10G:
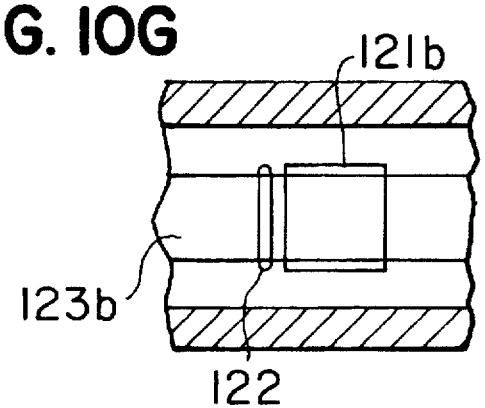
Figure 10H:
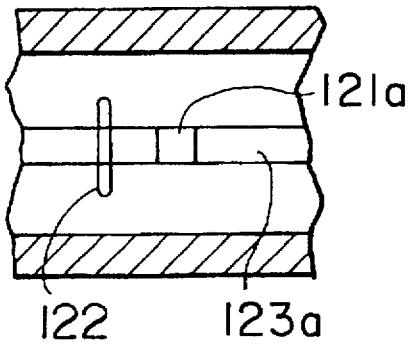

In the method shown in FIG. 10D, the width, the flow rate and the thickness of a sample flow 123 are switched between the low magnification mode and the high magnification mode. The width of the sample flow 123 is set to be slightly smaller than that of a photographing region 122 in either mode. The width of a detection region 122 is not changed even when the mode is changed.

The width, the thickness and the flow rate of the sample liquid are, in this case, determined as follows. In the high magnification mode, the sample liquid flows with its width slightly narrower than that of a photographing region 121a. The thickness of the sample liquid is made substantially coincide with the thickness which can be photographed with the microscope. In the low magnification mode, the sample liquid flows with its width slightly narrower than that of a photographing region 121b. The thickness of the sample liquid is made substantially coincide with the thickness which can be photographed with the microscope.

The measuring method shown in FIG. 10D has the following characteristic features. All the sample liquid discharged in the flow cell passes through the photographing region 121 in either mode, and therefore, the volume of the sample liquid passing through the photographing region can accurately be known. Since the detection region 122 is not required to be changed of its width, the optical system for detection can be simplified, the apparatus can be reduced in size and the adjustment procedure can be simplified. Further, as the sample liquid 123 uniformly flows over the entire width of the photographing region 121, the area of the photographing region 121 can effectively be used, and the analysis can efficiently be performed. Since the particles do not pass through the ends of the photographing region 121, the entire shape of the particles can be photographed, and the image analysis can accurately be performed.

Modifications of the flow cell will now be described with reference to FIGS. 11 to 17.

At the outset, a method of changing the flow of the sample liquid by means of the flow cell 1 of the apparatus according to the first embodiment will be described. According to the foregoing methods shown in FIGS. 10A to 10C, the width of the sample flow is not changed regardless of the magnification, but only the flow rate and the thickness are changed. In the flow cell 1 of the first embodiment shown in FIG. 6, the width of the sample liquid is determined depending upon the width of the guides 16 of the nozzle 3, and it is kept constant even if the flow rate of the sample fluid is changed. Therefore, increase in the flow quantity of the sample liquid causes the thickness of the sample flow to be increased while the width being kept constant. That is, in the case of the methods shown in FIGS. 10A to 10C, switching between the large magnification mode and the low magnification mode can be made relatively easily by adequately changing the flow quantity of the sheath liquid and that of the sample liquid.

Figure 11:
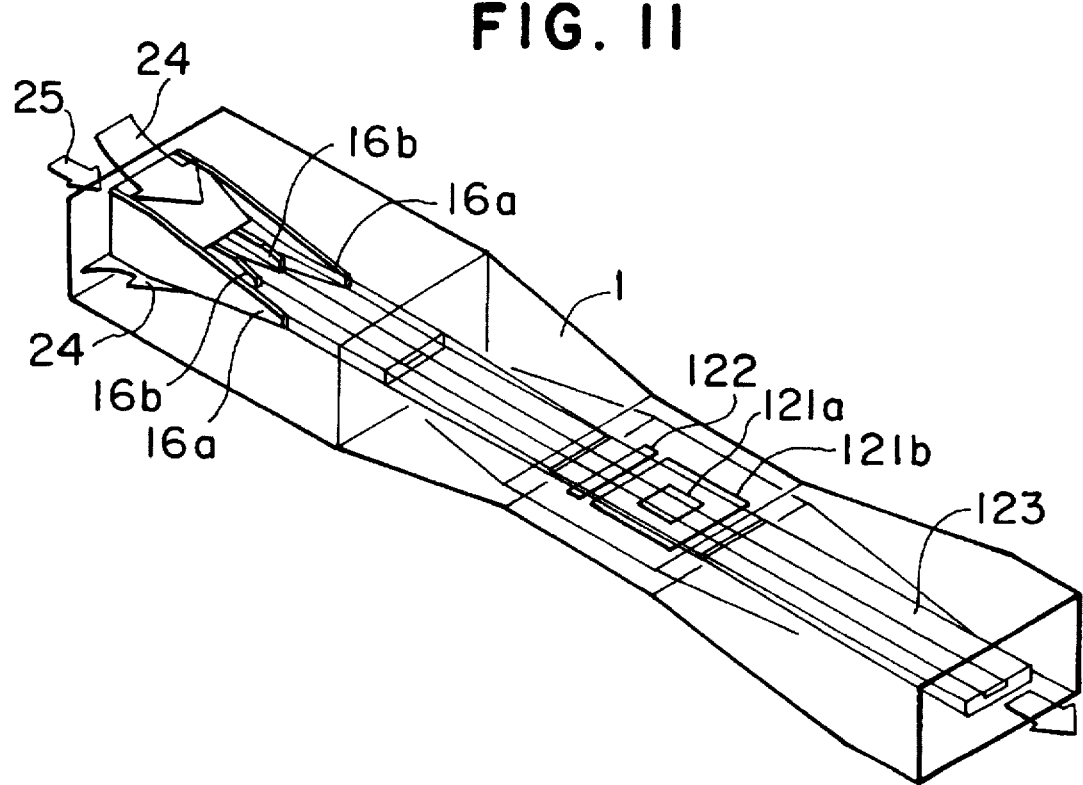
FIG. 11 is a schematic perspective view of a flow cell according to a modification for putting the method of FIG. 10D into practice.

In the method shown in FIG. 10D, it is necessary to change the width, the flow rate and the thickness of the sample flow depending upon the magnification. The flow cells shown in FIGS. 11 to 17 enable also the width of the sample flow to be varied. The flow cell shown in FIG. 11 is different in structure from the flow cell 1 according to the first embodiment in that double guides and double flow passages, both of which have different lengths, respectively, are provided on a nozzle. That is, on the inside of outer guides 16a, shorter guides 16b are disposed. In the case of a low magnification, a sample flow is formed with its width determined by the distance between the two outer guides 16a. When the magnification is large, another sample flow is formed with its width determined by the distance between the two inner guides 16b. The distances between the respective pairs of the guides are regulated to be adaptable to the width of the sample flow in the high magnification and to that in the low magnification. The widths of a photographing region, a detection region and the sample flow in a measuring portion are set as shown in FIG. 10D.

Figure 12:
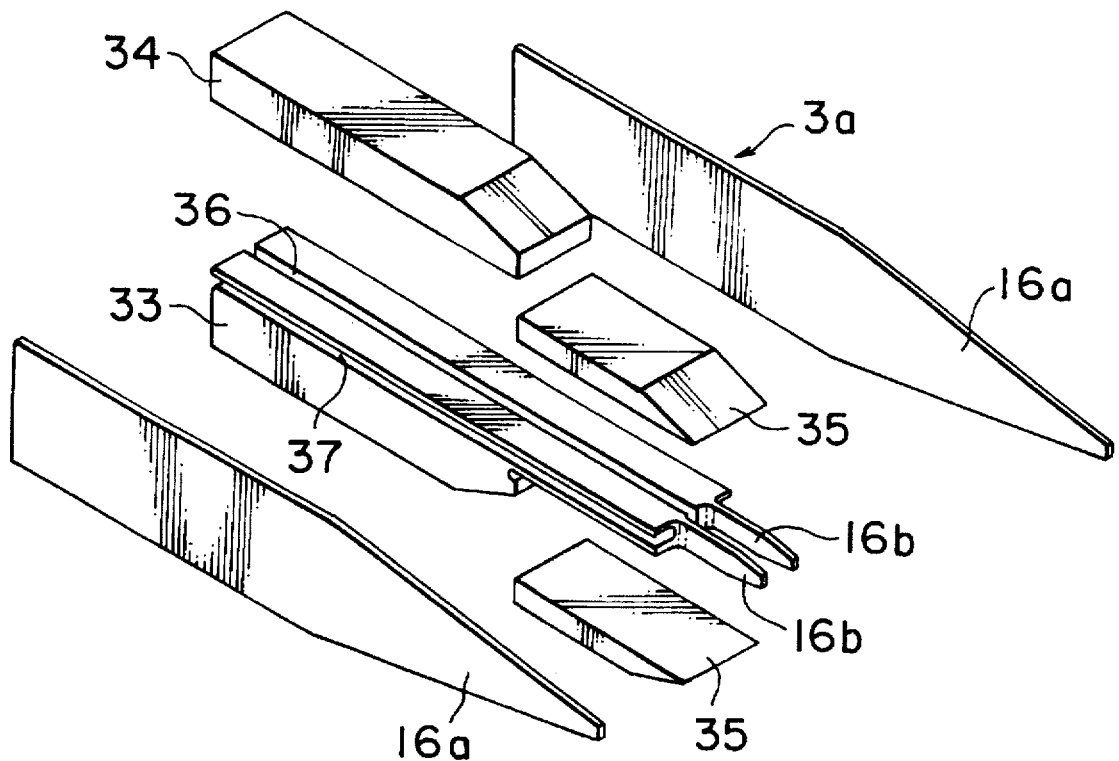
FIG. 12 is an exploded perspective view showing the structure of a nozzle in the flow cell of FIG. 11.

The structure of the nozzle 3a in which the double guides are provided will be described in detail with reference to FIG. 12. The nozzle 3a is composed of a main body 33 which is integrally formed with parallel guides 16b, covers 34 and 35 which are joined to upper and lower sides of the body 33, respectively, and a pair of parallel outer guides 16a which are joined to both lateral sides of the body, respectively. When a magnification is low, the sample liquid is allowed to flow through only a single fluid passage 36 which is formed in the body 33 to open between the two guides 16b, and the sample flow has a width which is equal to the distance between the inner guides 16b. When the magnification is high, the sample liquid is allowed to flow from both of the flow passage 36 and flow passages 37 which are formed in both sides of the body 33. Accordingly, the sample flow has a width which is equal to the distance between the two outer guides 16a. These the flow passages are switched under the control of electromagnetic valves (not shown in the figure) connected to the corresponding flow passages.

Figure 13:
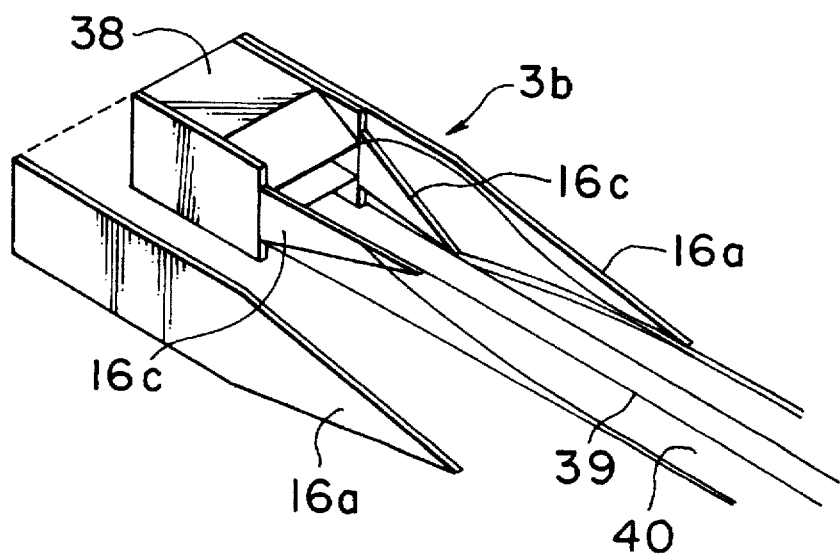
FIG. 13 is an exploded perspective view showing the structure of a nozzle according to another modification.

FIG. 13 shows a modification of the nozzle, in which only one sample passage is provided. The nozzle comprises a main body 38, inner guides 16C which are joined to both sides of the body 38 at an angle thereto, respectively, and guides 16a which are joined to the outsides of the guides 16C, respectively. That is, the nozzle 3b is composed of the pipe-like nozzle main body 38 which is in a hollow, square cross sectional shape, the pair of parallel, plate-like guides 16a which are respectively disposed on the both sides of an outlet port of the nozzle body 38, and the pair of plate-like guides 16C which are respectively disposed inside the parallel, plate-like guides 16a at the angle with their ends directed inwardly. When a magnification is low, the quantity of the sample flow is small, therefore, it flows along the inner guides 16C as indicated by reference numeral 39, and the width of the sample flow 39 is equal to the distance between the ends of the inner guides 16C. When the magnification is high, the quantity of the sample liquid flow is enlarged, therefore, it flows over tapered portions of the inner guides 16C to flow along the outer guides 16a, and the width of a sample flow 40 is equal to the distance between the outer guides 16a. The nozzle 3b shown in FIG. 13 has no necessity of switching the sample fluid passage, and the switching of the sample flow can be performed easily as compared with the nozzle 3a shown in FIG. 12.

Figure 14:
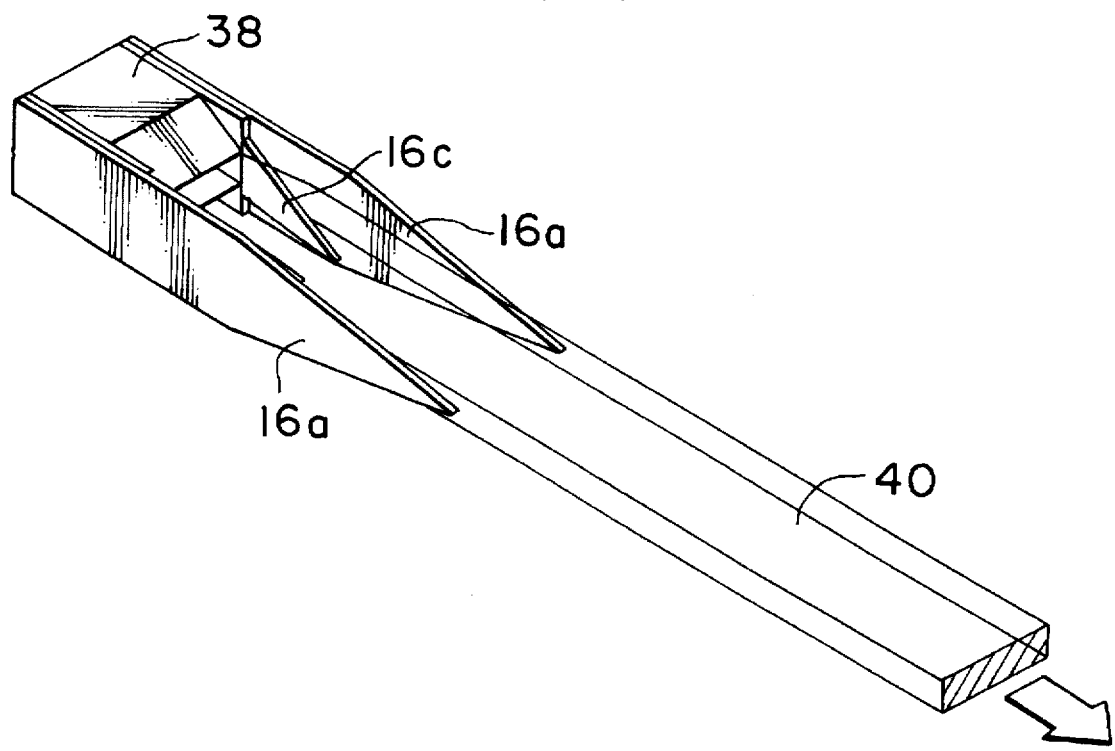
FIGS. 14 and 15 are perspective views showing flows of different shapes by the nozzle of FIG. 13, respectively.

Also in the case of the nozzle 3b shown in FIG. 13, similarly to the embodiments described above, the sample liquid is discharged from an outlet port in the end of the nozzle body 38. A sheath flow is formed in the flow passage, and the sample liquid flows at a constant speed through the flow passage. At this time, if the quantity of supply of the sample liquid is more than a predetermined level, the sample liquid flows from the outlet port in the end of the nozzle body 38 in such a manner that it moves over the inner guides 16C which are provided to be mutually inclined. The sample liquid, which has moved over the guides 16C, flows along the outer guides 16a as shown in FIG. 14. Therefore, the width of the sample flow 40 in the case depends upon the distance between the guides 16a.

Figure 15:
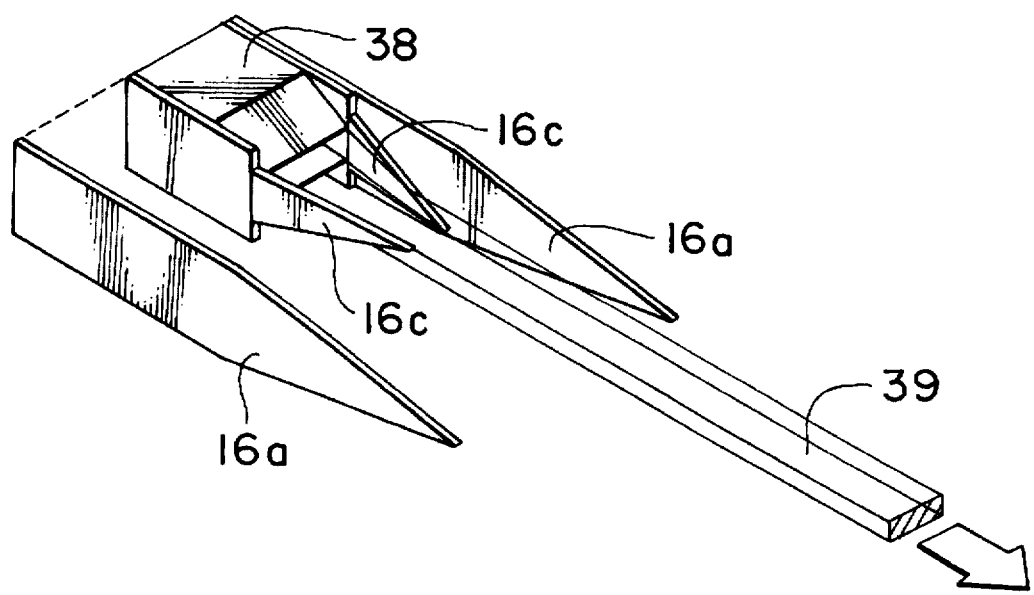

Similarly, the quantity of the flow of the sample liquid to be introduced through the sample liquid supply port is reduced during the examination or prior to beginning the examination of a next sample. This operation causes the sample liquid to flow along the inside of the guides 16C without moving over them as shown in FIG. 15. In this manner, the shape of the sample flow passing through the flow passage can be changed from the sample flow 40 shown in FIG. 14 to the sample flow 39 shown in FIG. 15. That is, the width of the sample flow can be controlled in two sorts by means of the flow quantity of the sample liquid. Further, when the quantity of the flow of the sheath liquid and that of the sample liquid are changed while keeping the ratio of them constant, only the flow rate can be controlled without changing the shape of the sample flow.

Figure 16:
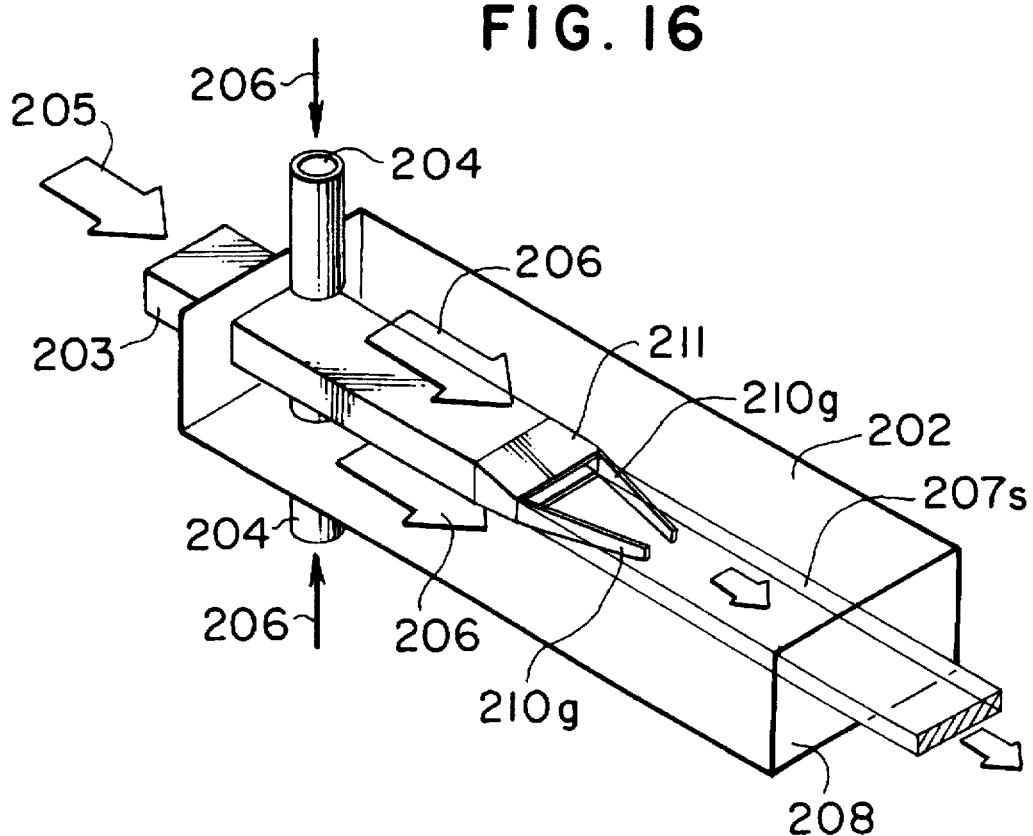
FIGS. 16 and 17 are schematic perspective views of a flow cell according to another modification, which show flows of different shapes in the flow cell, respectively.

FIG. 16 shows a flow cell according to another modification. The flow cell comprises a pipe-shaped nozzle 211 which has a hollow, square cross sectional shape, a pair of plate-like guides 210g which are disposed on both sides of an outlet port of the nozzle 211, respectively, a flow passage 202 and a sheath liquid supply port 204 connected to the flow passage 202. Each of the guides 210g is tapered to the tip thereof. The flow passage 202 is substantially constant in width and thickness and has a structure that a part thereof is formed of, for example, a glass so that the inside can optically be examined from outside. The flow passage 202 does not necessarily have to be rectangular in cross section and be in a straight hollow shape. It may be formed in, for instance, a cylindrical shape or a curved shape in accordance with the conditions of the flow cell. As an alternative, an enlarged or contracted passage, the cross sectional area of which is changed as is in the first embodiment, may be employed.

As shown in FIG. 16, a sample liquid 205 is supplied through a sample liquid supply port 203 and discharged from an outlet port in the end of the nozzle 211 into the flow passage 202 at a predetermined flow rate. On the other hand, a sheath liquid 206 is supplied through a sheath liquid supply portion 204 into the flow passage 202 at a predetermined flow rate. In the flow passage 202, the sheath liquid 206 flows to surround the sample liquid 205, so that a sheath flow which is a steady laminar flow is formed. The sample liquid 205 is formed into a sample flow 207s in the sheath flow to flow through the flow passage 202 at a constant speed. At this time, depending on the quantity of supply, the sample liquid 205 from the nozzle 211 moves over the guides 210g, which are disposed to be inclined inwardly toward each other, to flow over the entire width of the nozzle opening. The extent to which the sample flow gets over the guides 210g varies depending upon the flow rate of the sample liquid. The sample flow 207s is, together with the sheath liquid 206, introduced to the outside of the flow passage 202 through a waste fluid port 208.

The sample flow 207s passing through the flow passage 202 is subjected to an optical and non-contact examination measure, such as a laser beam source and a laser receiving element or a light source and an image recognition element, and the characteristics of the sample liquid 205 itself or those of particles contained in the sample liquid 205 are examined.

Figure 17:
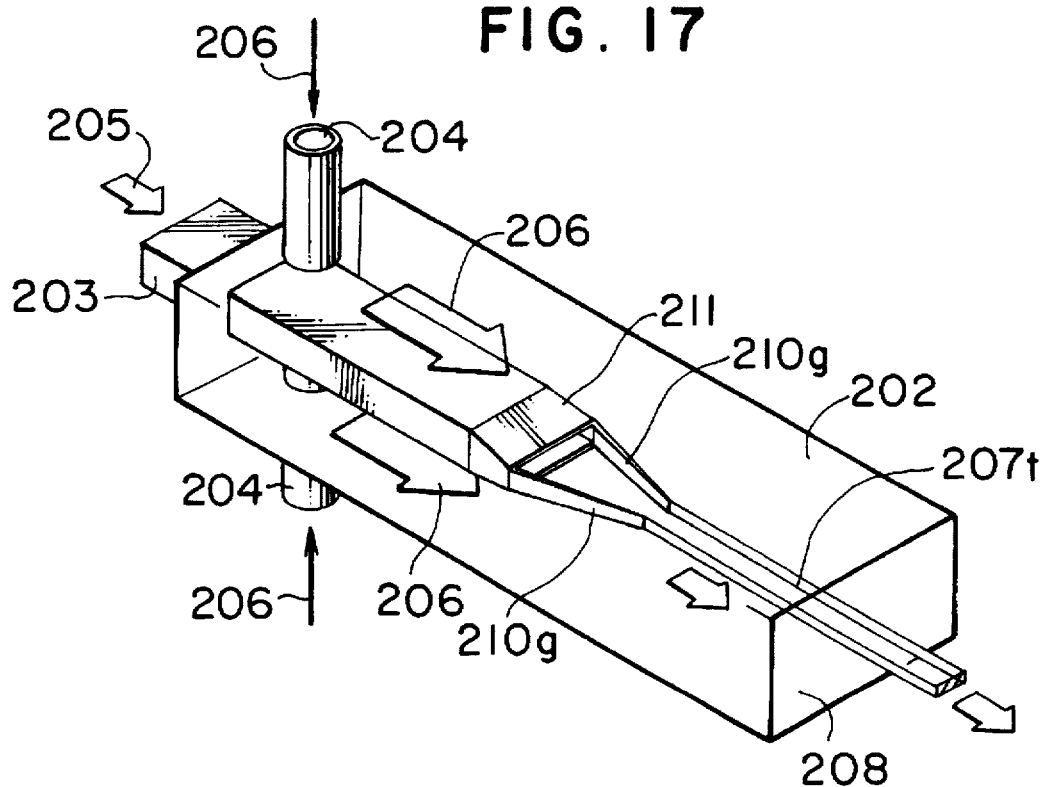

Similarly to the modifications shown in FIGS. 11 to 15, an operation for reducing the quantity of the sample liquid 205 to be supplied through the sample liquid supply port 203 may be made during the examination or prior to examining a next sample. By this operation, the sample liquid 205 from the nozzle 211 does not get over the guides 210g, but it flows inside the guides 210g as shown in FIG. 17. Through the adjustment of the quantity of the sample liquid flowing over the guides, the shape of the sample flow passing through the flow passage 202 can be changed from the sample flow 207s shown in FIG. 16 to a sample flow 207t shown in FIG. 17. That is, the width of the sample flow 207s can be controlled by adjusting the flow rate of the sample liquid 205. If the flow rate of the sheath liquid and that of the sample liquid are changed while keeping the ratio of them constant, only the flow velocity can be controlled without changing the shape of the sample flow.

The foregoing control enables sample flows to be successively formed in the same flow cell with their widths, thicknesses and flow speeds adapted to plural types of examination conditions. Therefore, the examination can be performed precisely, the flow passage system and the examination optical system can be simplified, the quantity of the sample required to perform the examination can be reduced and the time required to complete the examination can be shortened.

Further, sample flows having widths, thicknesses and flowing speeds which are suited for plural kinds of samples, respectively, can be successively formed in the same flow cell. Therefore, the examination can be carried out under the optimum conditions for the examination optical system, and the examination can be performed precisely.

Moreover, according to this modification it is possible to change the shape of the sample flow by only changing the flow rate of the sample liquid supplied to the single nozzle passage. Accordingly, the necessity of changing the shape or the position of a nozzle or changing the flow rates of a sample for plural passages can be eliminated, and the shape of the sample flow can easily be controlled.

Figure 18:
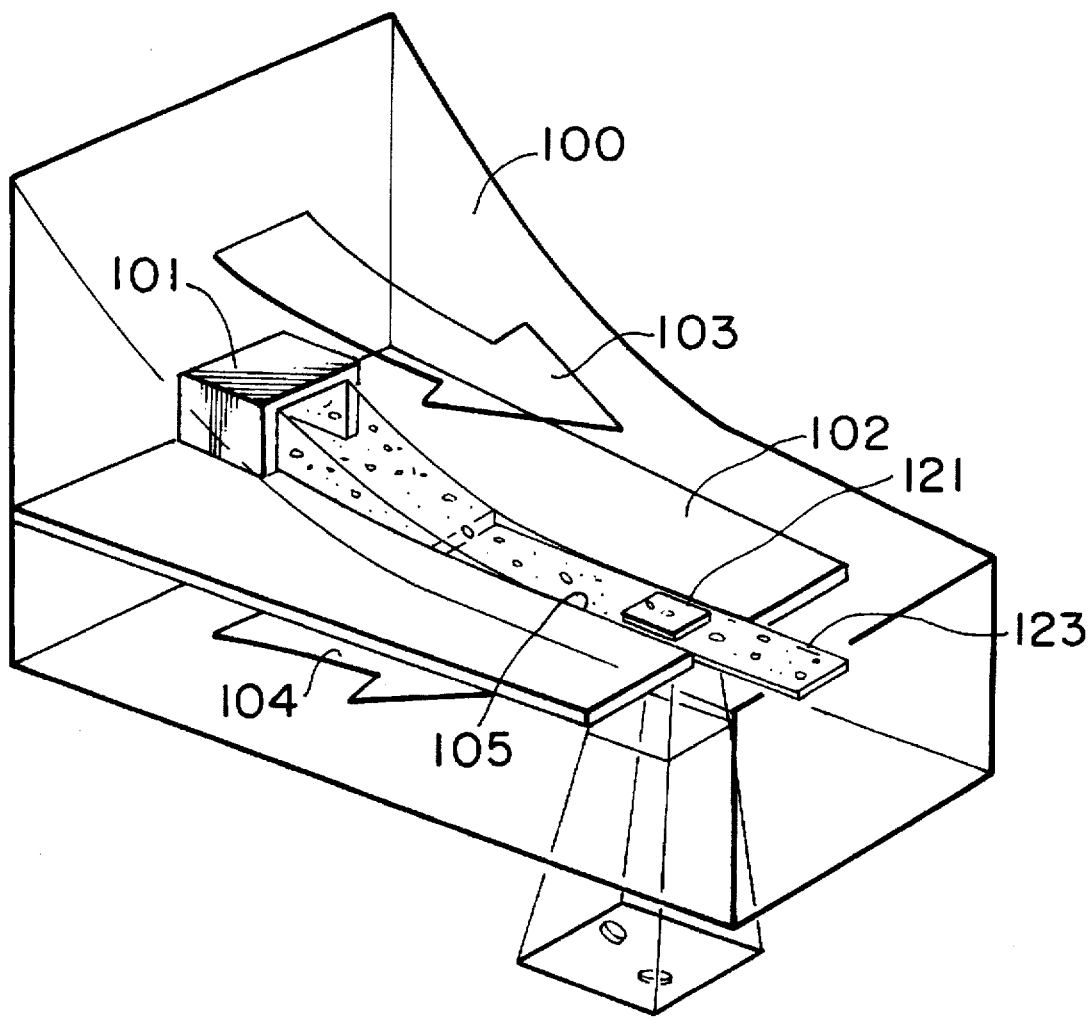
FIG. 18 is a schematic perspective view showing a flow cell according to another modification.

A flow cell according to still another modification will be described with reference to FIG. 18.

The flow cell of this modification has a flow passage 100, which is defined at its top and bottom by transparent plates so that an imaging region 121 for a sample flow can be observed. The fluid passage 100 is vertically divided into upper and lower portions by a guide plate 102 which extends across the flow passage 100. As shown in FIG. 18, the lower flow passage portion is constant in height, while the upper flow passage portion is partially reduced in height to form a flow reducing or contracting passage. A parallel fluid passage portion serving as a measuring portion follows the flow contraction passage. The width of the flow cell passage is made constant similarly to the foregoing embodiment and modifications. An upper sheath liquid 103 is caused to flow in the upper flow passage portion, and a lower sheath liquid 104 is introduced in the lower flow passage portion. A sample nozzle 101 is rectangular in its outlet cross section and is disposed on the guide plate 102. Further, the guide plate 102 is partially formed with a slit 105 at a position downstream from the nozzle 101. The sample discharged from the nozzle 101 is pushed against the guide plate 102 by the upper sheath liquid 103 while increasing its flow velocity to be formed into a flat sample flow 123. Then, the sample flow 123 is introduced into the slit 105 of the guide plate 102, and it is surrounded by the lower sheath 104 to form a sheath flow. The sample flow 123 in the sheath flow is shaped to have the width of the slit 105 and the thickness of the guide plate 102, and an accurate sheath flow can be realized.

Figure 19:
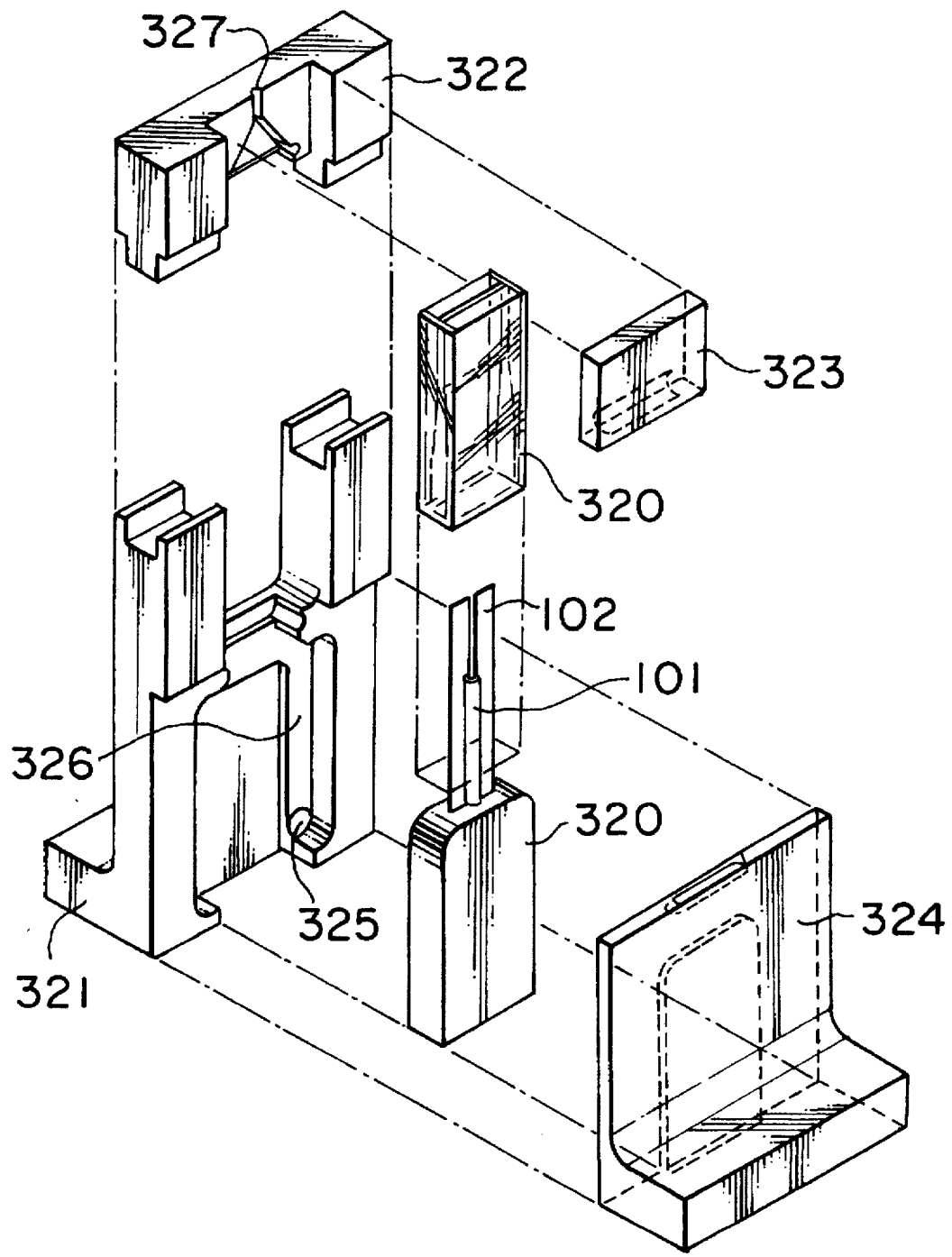
FIG. 19 is an exploded perspective view showing the structure of a flow cell of a flow cell apparatus according to a second embodiment of the invention, in which the flow cell shown in FIG. 18 is employed.

A flow cell apparatus according to a second embodiment of the invention will be described with reference to FIG. 19. This embodiment comprises a flow passage formed in a housing 302, which is similar to the flow passage shown in FIG. 18. The housing 302 is made of a transparent material such as glass so that a sample flow therein can be observed. The guide plate 102 and the nozzle 101 as described above are attached to a nozzle retainer 320. The nozzle retainer 320 has a sample passage formed therein. The housing 302 and the nozzle retainer 320 are secured by means of holder upper portions 322, 323 and holder lower portions 321, 324. The holder lower portion 321 is provided with a sheath liquid passage 326 and a sheath liquid inlet port 325, while the holder upper portion 322 is provided with a waste liquid port 327. With the structure thus formed, similar effect and function to those of the foregoing embodiment can be achieved.

Various modifications of the flow cell in the flow cell apparatus according to the invention will be described with reference to FIGS. 20 to 29. These flow cells of the modifications are each applicable also to either the first embodiment or the second embodiment.

Figure 20:
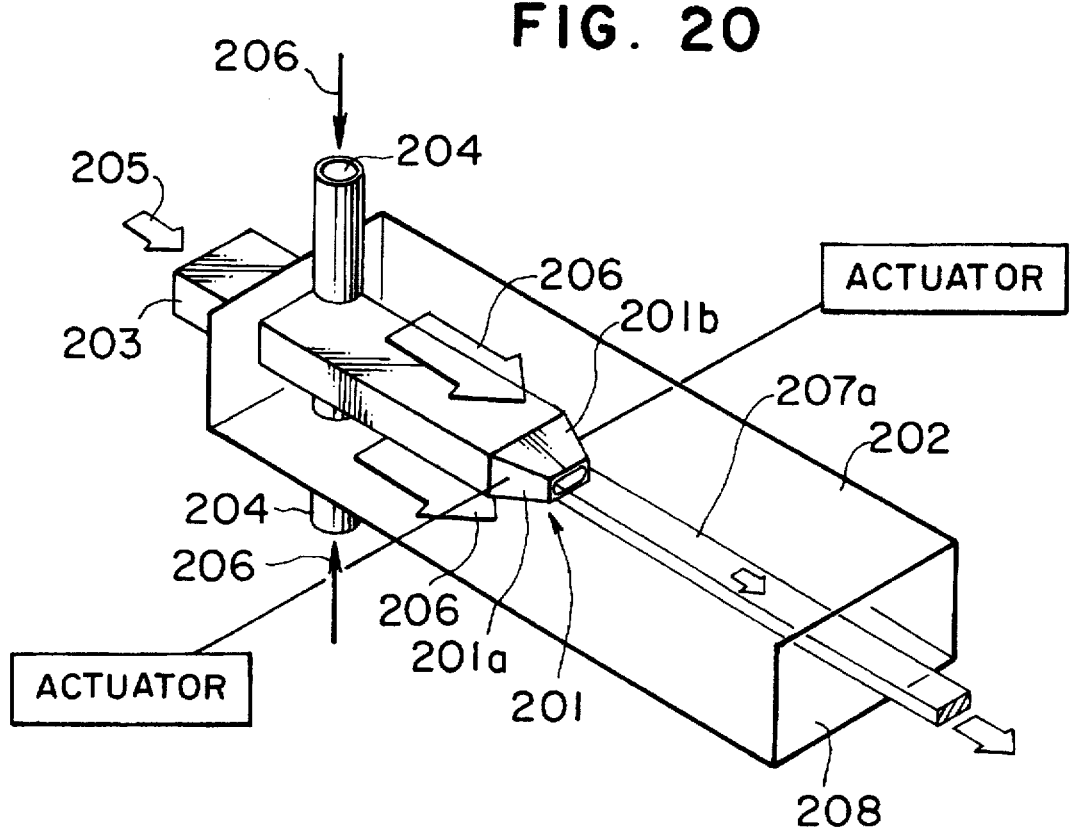
FIGS. 20 and 21 are schematic perspective view of a flow cell according to a modification that is applicable to both the first embodiment and the second embodiment, which show flows of different shapes in the flow cell, respectively.
Figure 21:
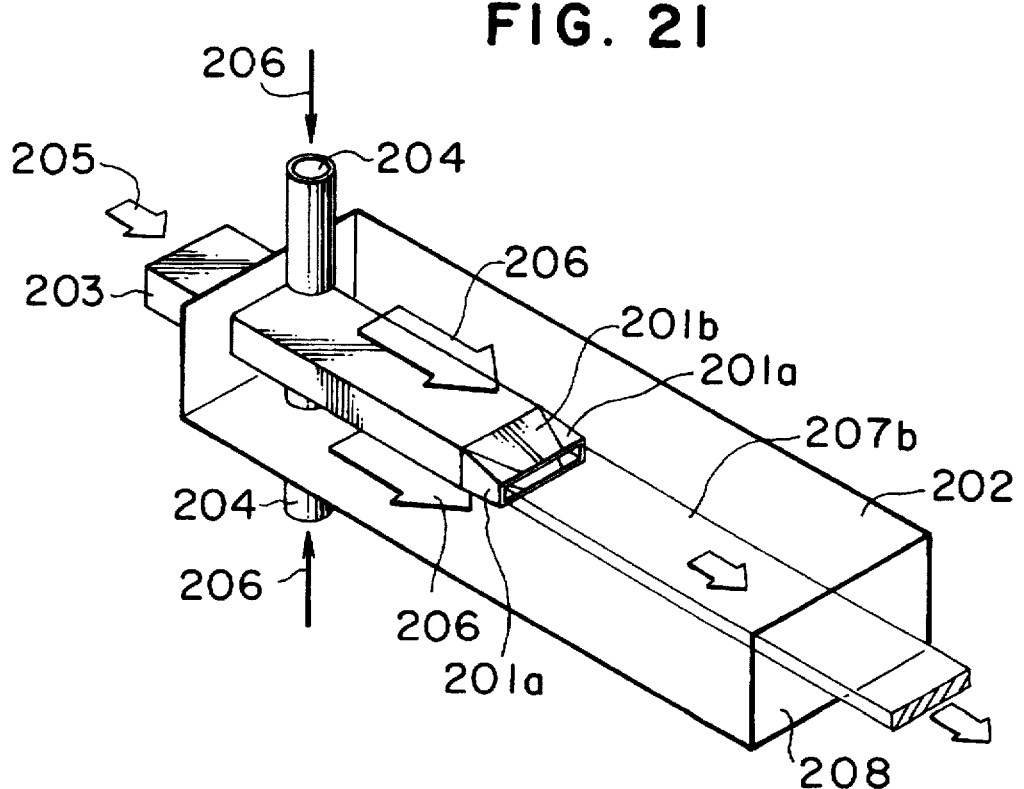

A flow cell shown in FIGS. 20 and 21 is so constructed that the opening of a nozzle 201 is variable in width. The nozzle 201 is formed in a hollow shape which has a rectangular cross section and is reduced in height toward its opening end. The nozzle 201 has two side portions 201a which are provided for movement toward or away from a central portion 201b of the nozzle. The two side portions 201a are operatively connected to actuators, respectively, which are disposed on the outside of the flow cell. The other component parts of the flow cell of FIGS. 20 and 21 are the same as those of the modification shown in FIGS. 16 and 17, and the same reference numerals are given to the other component parts to omit the description thereof.

FIG. 20 shows a state where the two side portions 201a of the nozzle 201 have been moved inwardly by the driving of the actuators, and the width of the opening of the nozzle 201 has been decreased. At this time, the sample fluid 205 supplied through the supply port 203 is formed in the flow passage 202 into a columnar sample flow 207a which has a cross sectional shape like the shape of the opening end of the nozzle 201.

The nozzle 201 may be operated in such a manner that the two side portions 201a are moved outwards from the central portion 201b to change the shape of the opening of the nozzle 201 during an examination or prior to performing an examination of the next sample. That is, the width of the opening of the nozzle can be varied from, for example, about 700 μm to about 200 μm. The flow rate of the sample liquid and that of the sheath liquid may be changed simultaneously. As a result of the foregoing operations, the shape of the sample liquid flowing through the flow passage 202 can be changed from the sample flow 207a shown in FIG. 20 to a sample flow 207b shown in FIG. 21.

In other words, since the cross sectional shape of the sample flow is changed depending upon the shape of the opening of the nozzle, the control of the shape of the opening of the nozzle enables the width of the sample flow to be changed from, for example, about 700 μm to about 200 μm. Further, when the flow rate of the sheath liquid and that of the sample liquid are changed while keeping the ratio of them constant, only the flowing speed of the sample can be controlled without altering the shape of the sample flow. The flow cell of this modification has an advantage which is similar to that of the modification shown in FIGS. 16 and 17.

Also in modification shown in FIGS. 22 to 25, nozzles are so formed as to be able to vary the widths of their openings. Flow passages and associated component parts of these modifications are the same as those of the modification shown in FIGS. 20 and 21, and only the nozzles are shown in FIGS. 22 to 25. The nozzle shown in FIG. 22 comprises a tube 209 which serves as a passage for a sample liquid and is made of an elastic material, and two movable nozzle retaining plates 201C disposed to clamp the tube 209, from both sides thereof.

A sample liquid is supplied through the sample liquid supply port 203 and discharged from an end of the tube 209 into the flow passage at a predetermined flow rate, and it is formed into a sample flow 207c in the sheath flow to flow in the flow passage at a constant flow velocity. The sample flow 207c is, at this time, in a columnar shape which has a cross section resembling the shape of the end of the tube 209.

Figure 22:
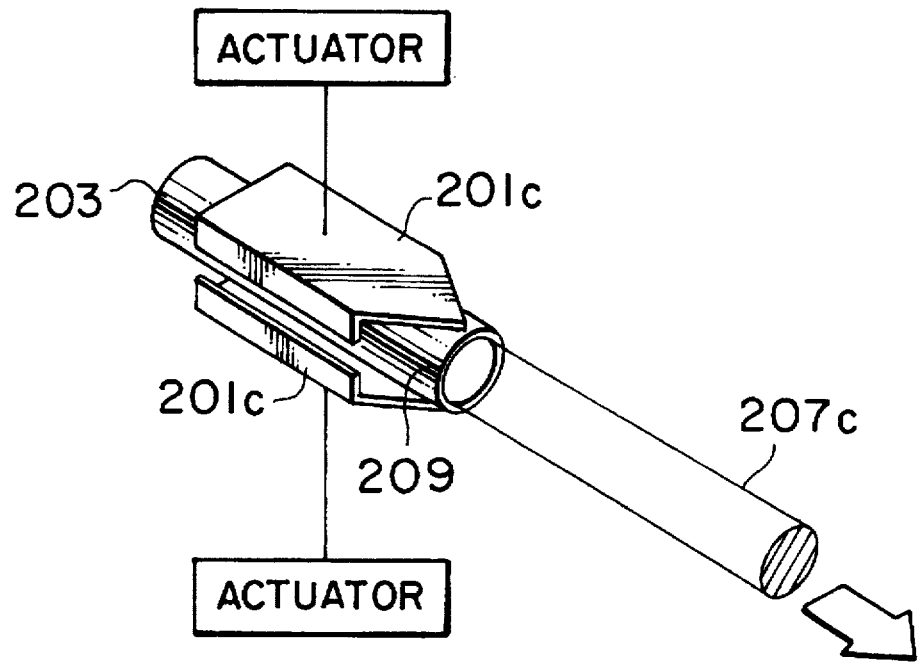
FIGS. 22 and 23 are perspective views of a nozzle according to another modification, which show flows of different shapes in the flow cell, respectively.
Figure 23:
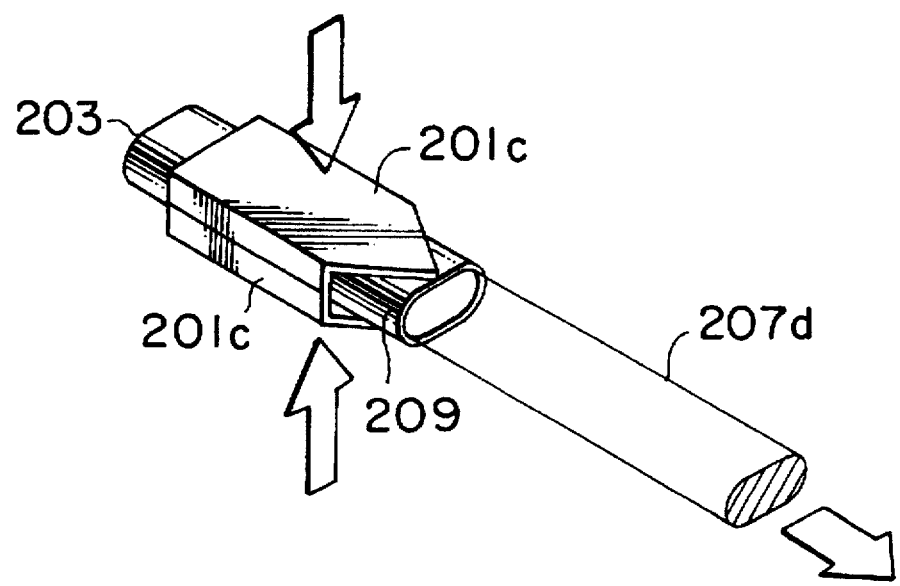

The nozzle shown in FIG. 22 can vary the shape of its end during an examination or prior to the examination of a next sample by clamping the tube 209 with the nozzle retaining plates 201C to elastically deform the tube 209. The nozzle retaining plates 201C are driven by actuators which are disposed on the outside of the flow cell. As a result of the above operation, the shape of the sample flow can be changed from the sample flow 207c of the columnar shape shown in FIG. 22 to a sample flow 207d of an elliptic shape shown in FIG. 23.

By changing the shape of the sample flow as described above, it is possible to achieve meritorious results which are similar to those attained by the modification shown in FIGS. 20, 21.

Figure 24:
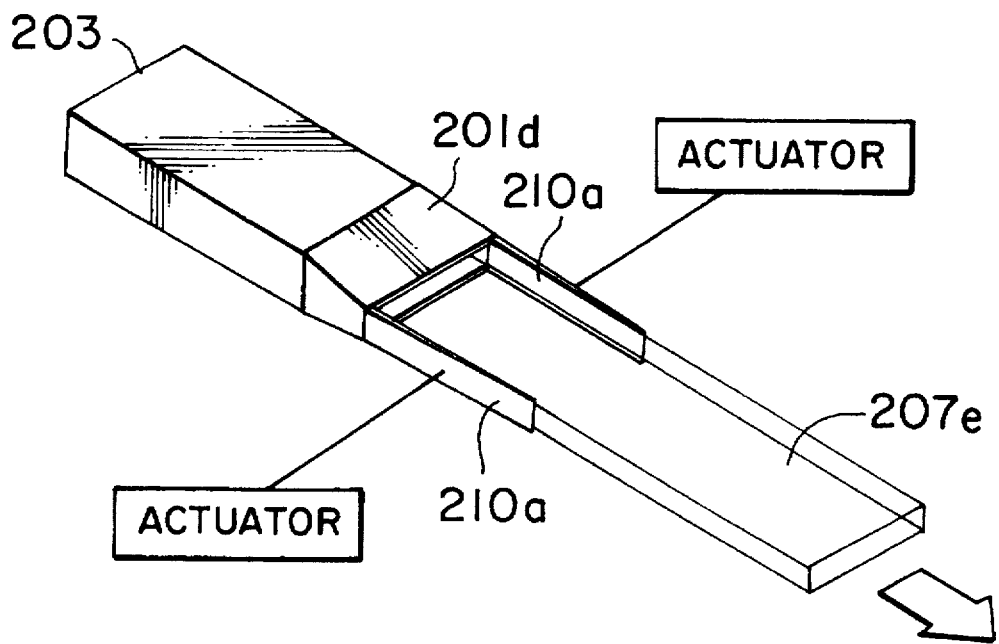
FIGS. 24 and 25 are perspective views of a nozzle according to still another modification, which show flows of different shapes in the flow cell, respectively.
Figure 25:
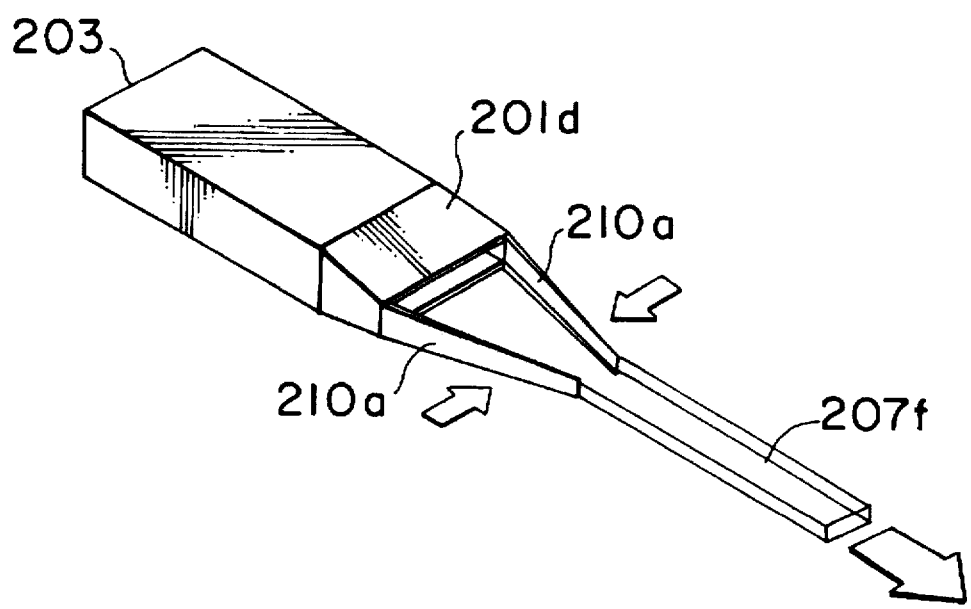

A nozzle 201d shown in FIGS. 24 and 25 is in a hollow shape which has a rectangular cross section and is reduced in height toward the end of an opening thereof. The nozzle 201d has two plate-like movable guides 210a on both sides of its sample liquid outlet.

A sample liquid is supplied through the sample liquid supply port 203 and discharged into the flow passage through the outlet port of the nozzle 201d at a predetermined flow rate. In the flow passage, the sheath liquid flows to surround the sample liquid, and a sheath flow which is a steady laminar flow is formed. The sample liquid forms a sample flow 207e in the sheath flow to flow through the flow passage at a constant flow speed. At this time, the sample flow 207e is in a columnar shape which has a cross section resembling the shape of the end of the nozzle 201d. Further, since the sample flow 207e passes along the two guides 210a, it can scarcely suffer from turbulence at the end of the nozzle 201d at which the sample liquid and the sheath flow join together. Therefore, a stable sample flow can be formed.

The nozzle 201d shown in FIG. 24 can move the guide 210a as indicated by arrows in FIG. 25 to vary the distance between ends of the guides during an examination or prior to the examination of another sample. The guides 210a are driven by actuators which are disposed at the outside of the flow cell. In the case where the nozzle is very small and it must be operated precisely, it is preferable that a drive mechanism, such as an electrostrictive actuator, a shape memory alloy or the like, is provided in the nozzle. This can be said also of the modifications shown in FIGS. 20 to 23. The guides 210a can vary the distance between ends thereof from, for instance, about 700 μm to about 200 μm. Further, the flow rate of a sample and that of a sheath liquid may be changed simultaneously with the deformation of the nozzle. With the above operation, the shape of the sample flow can be changed from a wide sample flow 207e shown in FIG. 24 to a narrow sample flow 207f shown in FIG. 25. Thus changing the shape of the sample flow, meritorious results similar to those achieved by the modifications shown in FIGS. 20 to 23 can be obtained.

Modifications shown in FIGS. 26 to 29 are structured in a manner that a nozzle can vary the shape of a sample flow. Flow passages and associated component parts of the modifications are the same as those of the modifications shown in FIGS. 20 to 25, and only nozzles are shown in FIGS. 26 to 29.

Figure 26:
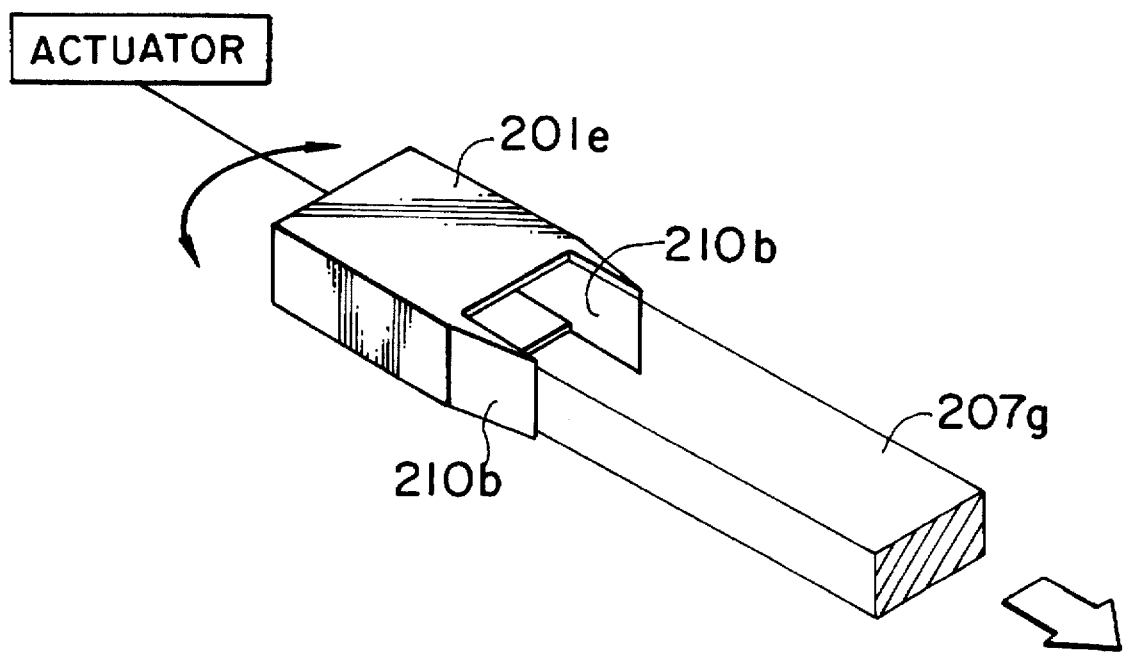
FIGS. 26 and 27 are perspective views of a nozzle according to still another modification, which show flows of different shapes in the flow cell, respectively.

A nozzle 201e shown in FIG. 26 has a hollow shape of a rectangular cross section and is movably mounted in the flow passage to be rotatable around its longitudinal axis. The nozzle 201e has a pair of guide plates 210b integrally formed on respective outer sides of its sample liquid outlet. A sample liquid is, similarly to the foregoing modifications, discharged through the nozzle 201e into the flow passage at a predetermined rate so that it forms a sample flow 207g in a sheath flow to flow at a constant velocity. The sample flow 207g is a columnar flow which has a cross section similar to the shape of the outlet port of the nozzle 201e. The sample liquid discharged from the nozzle 201e flows along the guides 210b, and it can hardly suffer from turbulence at a junction of the nozzle outlet port where the sample flow and the sheath flow join together. Therefore, a stable flow can be formed.

Figure 27:
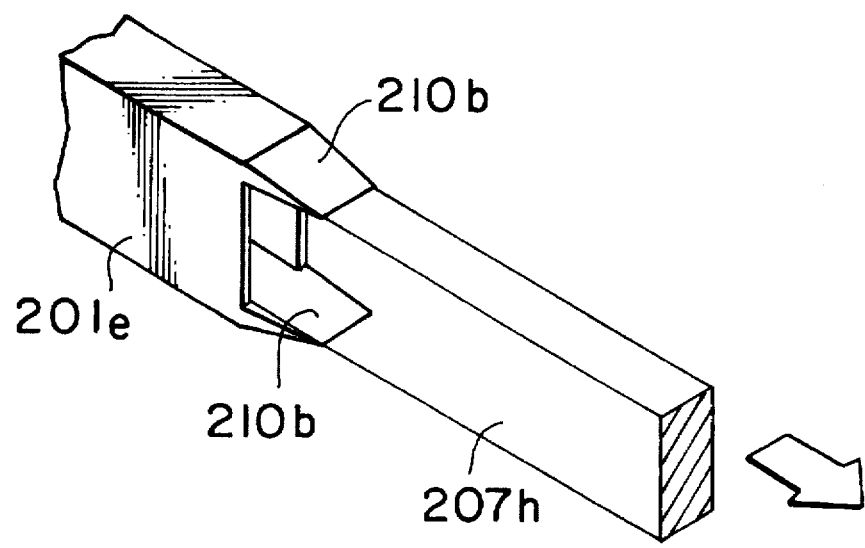

The nozzle 201e can be rotated by an angle of 90° from the state shown in FIG. 26 as shown in FIG. 27 during an examination or prior to another examination of the next sample. The nozzle 201e is driven by actuators which disposed at the outside of the flow cell. The flow rate of the sample liquid and that of the sheath liquid may be changed simultaneously with the rotation of the nozzle. With this operation, the sample liquid is changed from a flow 207g shown in FIG. 26 to a flow 207h shown in FIG. 27 which is different in the aspect ratio of cross section from the flow of FIG. 26. By thus changing the shape of the sample flow, this modification can achieve meritorious results which are similar to those attained by the modifications shown in FIGS. 20 to 25. That is, according to this modification, the selective rotation of the nozzle changes the aspect ratio of the cross section of the sample flow in accordance with the aspect ratio of the outlet shape of the nozzle, and therefore, a sample flow suitable to an examination can be obtained. When the flow rate of the sample liquid and that of the sheath liquid are changed while keeping the ratio thereof constant, only the flow velocity can be controlled without varying the shape of the sample flow.

Figure 28:
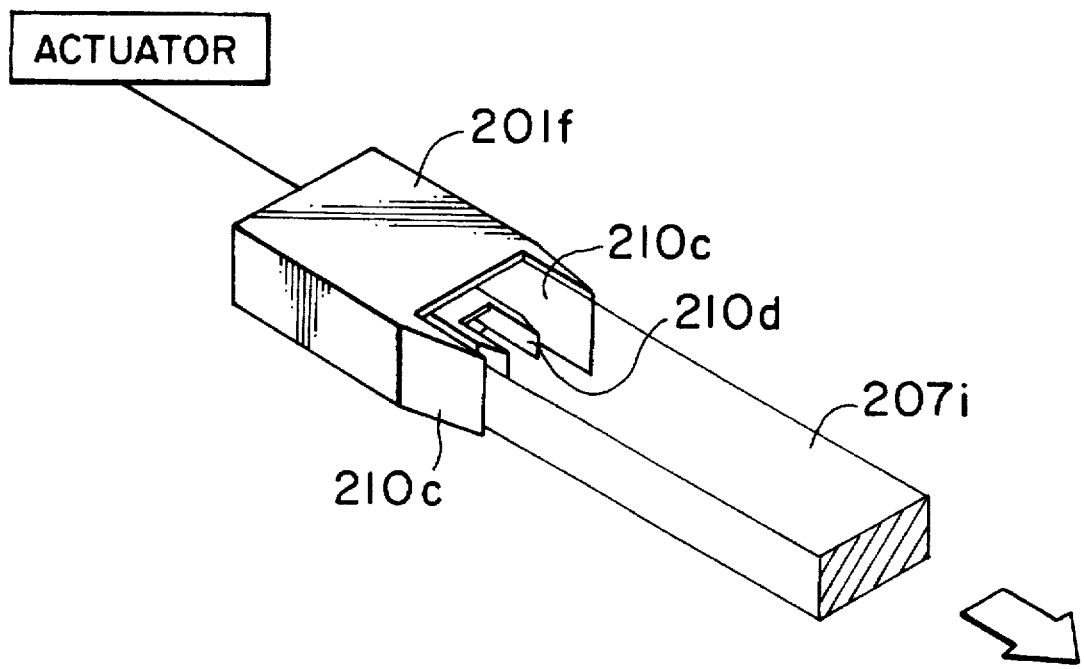
FIGS. 28 and 29 are perspective views of a nozzle according to still another modification, which show flows of different shapes in the flow cell, respectively.
Figure 29:
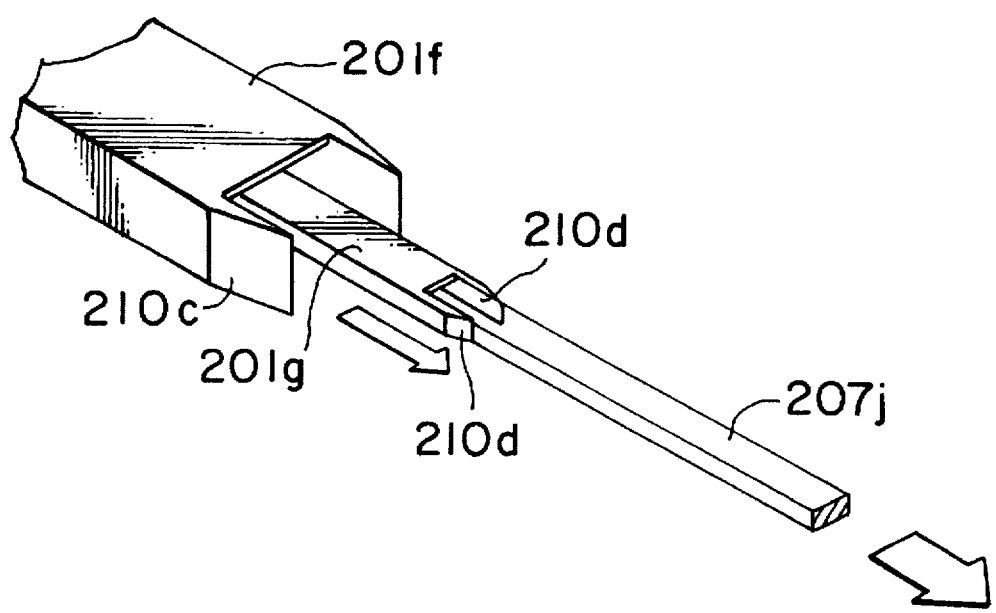

A modification shown in FIGS. 28 and 29 comprises two nozzles 201f and 201g. These nozzle are both in a hollow shape of a rectangular cross section. The nozzle 201g is smaller in configuration than the nozzle 201f, and is coaxially disposed in the nozzle 201f. The nozzle 201f has a pair of guide plates 210c integrally formed on respective outer sides of its outlet port for a sample liquid. Similarly, the nozzle 201g has a pair of guide plates 210d formed integrally. The nozzle 201g is movably mounted to be moved in a telescopic manner with respect to the nozzle 201f by the driving of actuators which are disposed at the outside of the flow cell.

In the state shown in FIG. 28, a sample liquid is discharged from the nozzles 201f and 201g at a predetermined flow rate, and it forms a sample flow 207i in a sheath flow to flow at a constant flow velocity. The sample flow is a columnar flow which has a cross section resembling the shape of the outlet port of the nozzle 201f.

According to this modifications, the actuators may be operated to cause the nozzle 201g to project from the nozzle 201f into the flow passage of the flow cell in parallel to the direction of the flow. In this case, an electromagnetic valve, which is connected to a liquid passage for the nozzle 201f, is closed so that the sample liquid is discharged through only the nozzle 201g. When the nozzle is very small and needs precisely driving, a drive mechanism, such as an electrostrictive actuator, a shape memory alloy or the like, may be provided. This can be said also of the modification shown in FIGS. 26 and 27. Further, the flow rate of the sample liquid and that of the sheath liquid may be changed simultaneously with the projection of the nozzle 201g.

As a result of the above operation, the shape of the sample flow is changed from the column shape shown in FIG. 28 to another flow of a smaller cross section shown in FIG. 29. This modification also can vary the shape of the sample flow to attain meritorious results which are similar to be obtained to that obtainable from the modification shown in those achieved by the modification of FIGS. 26 and 27. In either nozzle 201f or 201g, the sample liquid discharged therefrom flows along the guides 210c or 210d, and it can hardly be subjected to turbulence at a junction of the nozzle outlet port where the sample and the sheath liquid join together, and a stable flow can be formed.

Further modification of the flow cell in the flow cell apparatus of the invention will now be described with reference to FIGS. 30 to 37. Flow cell passages and related component parts of these modifications may be the same as those of the modification shown in FIG. 16. Only FIGS. 30 and 31 show the overall structure of the flow cell, and the other figures show nozzles alone.

Figure 30:
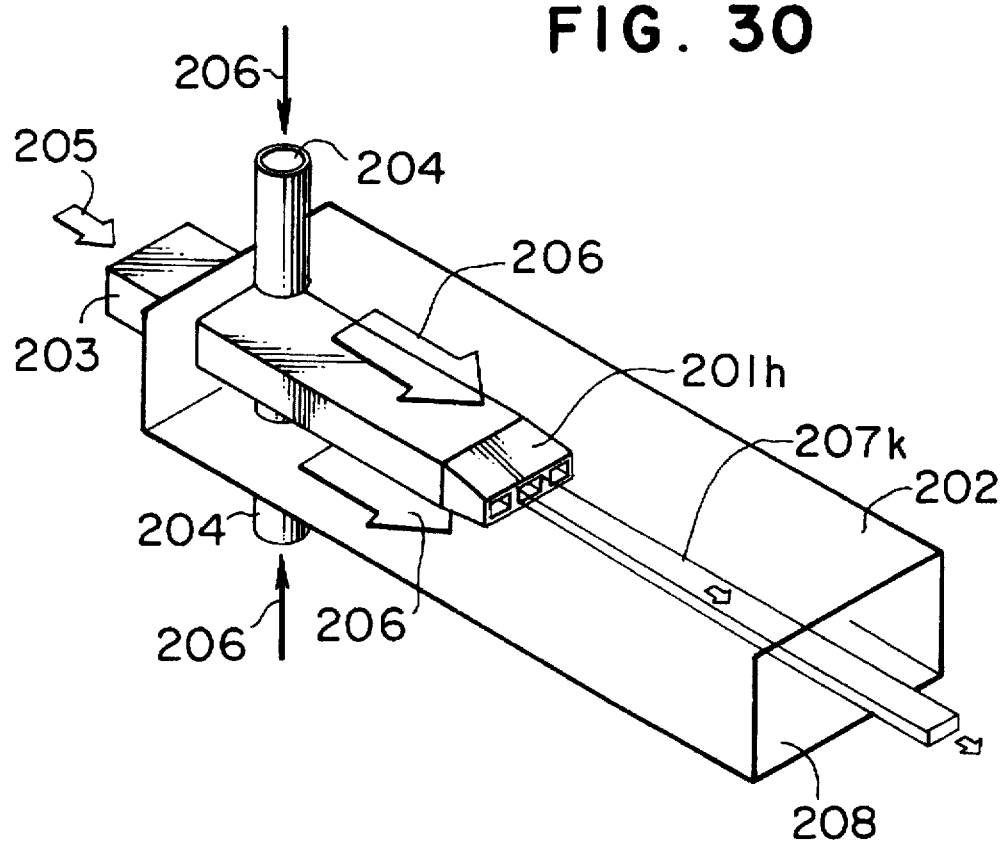
FIGS. 30 and 31 are schematic perspective views of a nozzle according to still another modification, which show flows of different shapes in the flow cell, respectively.

According to the modification shown in FIG. 30, the flow cell comprises a nozzle 201h which is composed of three hollow pipes, three sample liquid supply ports 203 communicating with respective pipe outlet ports of the nozzle 201h, a flow passage 202 surrounding the nozzle 201h, and a sheath liquid supply port 204 connected to the flow passage 202. The pipes of the nozzle 201h each have a rectangular cross section and are disposed side by side. Further, electromagnetic valves not shown in the figures are provided to be connected to the supply ports 203 on both sides of the nozzle 201h, respectively.

In the state shown in FIG. 30, a sample liquid is supplied to only central one of the three sample liquid supply ports 203, and it is discharged from the central outlet port of the nozzle 201h into the flow passage 202 at a predetermined flow rate. The other supply ports 203 are closed through the operation of the foregoing electromagnetic valves. On the other hand, a sheath liquid 206 is supplied from the sheath liquid supply portion 204 into the flow passage 202 at a predetermined flow rate. As a result, the sheath liquid 206 flows through the flow passage 202 while surrounding the sample liquid 205, and they form a sheath flow which is a steady laminar flow. The sample liquid 205 is formed into a sample flow 207k in the sheath flow and flows through the flow passage 202 at a constant flow velocity. The sample flow 207k has a columnar shape which has a cross section alike the shape of the central outlet port of the nozzle 201h. The sample flow 207k, together with the sheath liquid 206, is introduced through the waste fluid port 208 to the outside of the flow passage 202. At this time, an optical, non-contact inspection means, such as a laser light source and a laser beam receiving device or a light source and an image recognition device, is used with respect to the sample flow 207k which is flowing in the flow passage 202, so that the characteristics of the sample liquid 205 itself or particles contained in the sample liquid 205 are examined.

Figure 31:
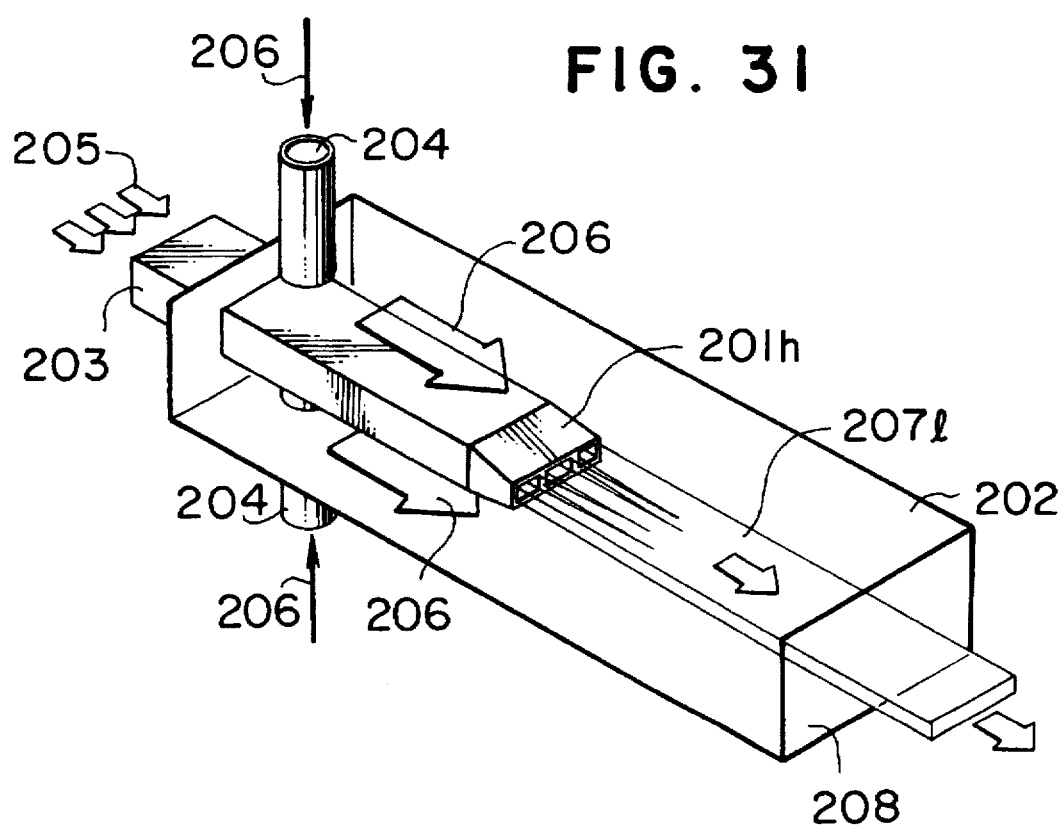

In case of wishing to change the width of the sample flow during an examination or prior to another examination of the next sample, as shown in FIG. 31, the sample liquid 205 is introduced through the sample liquid supply port 203 into all the three passages arranged in the nozzle 201h, and it is discharged from all the three outlets of the end of the nozzle 201h into the flow passage 205 at a predetermined flow rate. At this time, the flow rate of the sample and that of the sheath liquid may be changed simultaneously. With the above operation, the sample flow passing through the flow passage 202 can be changed in shape from a sample flow 207k shown in FIG. 30 to a sample flow 271 shown in FIG. 31. That is, the cross sectional shape of the sample flow can be changed by shifting the position for discharging the sample among the three liquid passages of the nozzle. Changing the flow rate of the sheath liquid and that of the sample liquid while keeping the ratio thereof constant, only the flow velocity can be controlled without altering the shape of the sample flow.

By virtue of the foregoing control, sample flows having widths, thicknesses and flow rates adaptable to plural examination conditions can successively be formed in the same flow cell.

According to this modification, particularly, since the shape of the sample flow is changed by simply changing the flowing conditions of the sample passing through the three liquid passages, there is no necessity of changing the shape and the position of the nozzle, and the nozzle can easily be made. Further, by introducing samples of different types from the respective liquid passages formed in the nozzle, the plural samples can simultaneously be measured. The number of the liquid passage is not limited solely to three, but it may be an arbitrary number.

Figure 32:
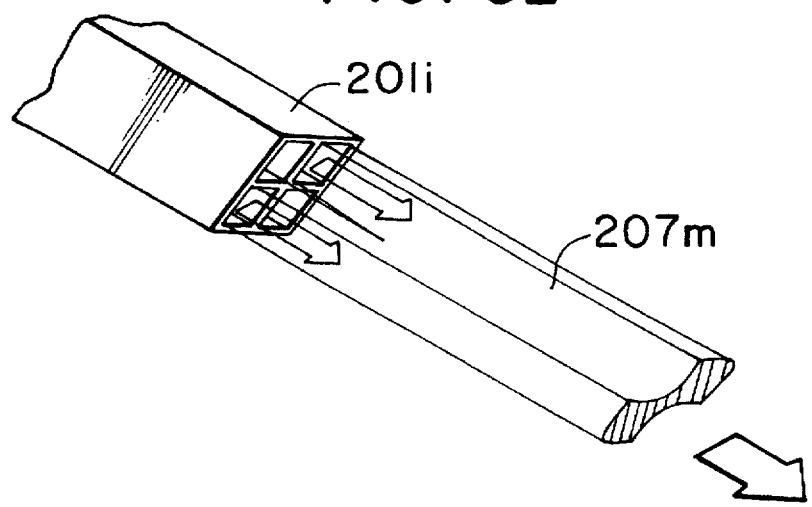
FIGS. 32 to 34 are perspective views of a nozzle according to still another modification, which show flows of different shapes in the flow cell, respectively.

A nozzle 201i according to a modification shown in FIG. 32 has liquid passages formed by four hollow pipes which are provided adjacently around a common axis and each have a substantially rectangular cross section. In this modification, when a sample liquid is supplied to two diagonally opposing nozzle passages and discharged from two outlet ports at the end of the nozzle 201i at a predetermined flow rate, it forms a sample flow 207m in a sheath flow to flow through the flow passage at a constant flow velocity. The sample flow 207m has a cross section of a columnar shape that is similar to the combined shapes of the two outlet ports at the end of the nozzle 201i through which the sample is being discharged.

Figure 33:
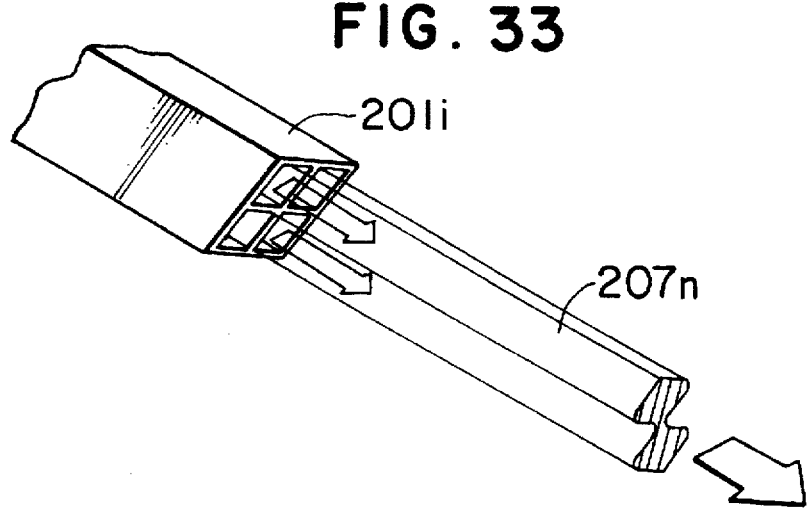
Figure 34:
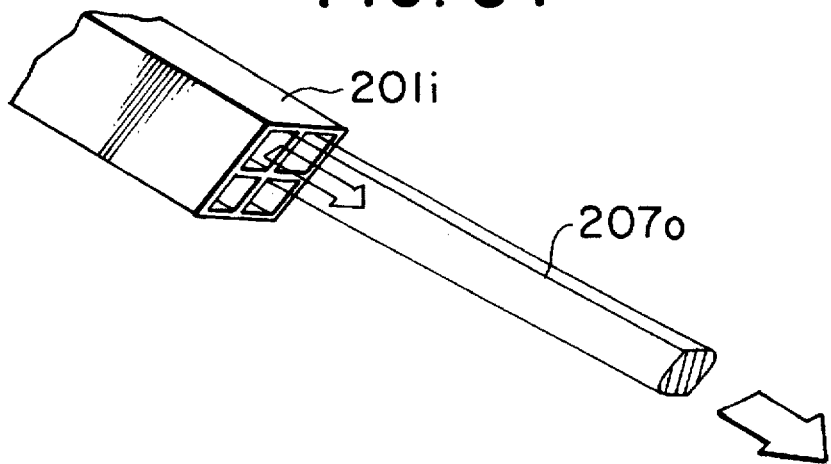

The liquid passages in the nozzle 201i for supplying the sample liquid can be changed as shown in FIG. 33 or 34 during an examination or prior to another examination of the next sample to vary the positions of the outlet ports at the end of the nozzle 201i for discharging the sample. The flow rate of the sample and that of the sheath liquid may be changed simultaneously. With this operation, the sample flow passing in the flow passage is changed in shape from a sample flow 207m shown in FIG. 32 to a sample flow 207n shown in FIG. 33 or to a sample flow 207o shown in FIG. 34. Thus changing the shape of the sample flow, it is possible to attain meritorious results which are similar to those achieved by the foregoing modifications. The change of the nozzle liquid passages is performed through the control of electromagnetic valves (not shown in the figures) which are connected to the respective liquid passages.

Figure 35:
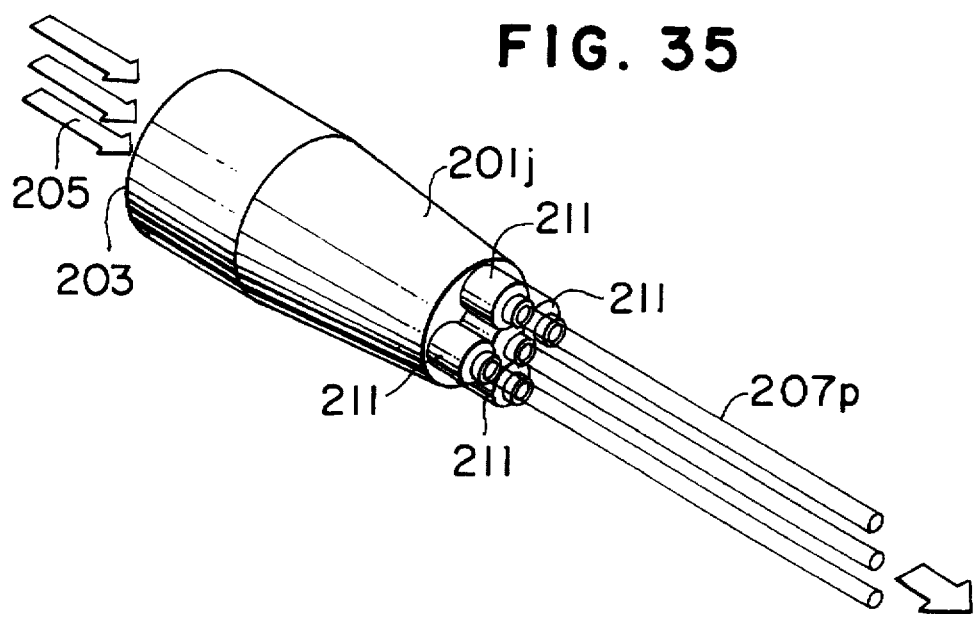
FIG. 35 is a perspective view of a nozzle according to still another modification.

A nozzle 201j according to a further modification shown in FIG. 35 has five liquid passages and five discharge ports 211 which are respectfully connected to the liquid passages and each have a circular cross section. The discharge ports 211 are arranged in such a manner that four discharge ports are situated around a central port at equal intervals. In the state shown in FIG. 36, a sample liquid 205 is supplied to upper, middle and lower liquid passages to be discharged through corresponding three sample discharge ports 211 of the nozzle 201 at a predetermined flow rate, and it forms a sample flow 207p in a sheath flow to flow through the flow passage at a constant flow velocity. At this time, the sample flow 207p has a cross sectional shape in the flow passage, which is alike the combined shape of the three sample discharge ports 211 from which the sample liquid is being discharged at the end of the nozzle 201j.

Similarly to the foregoing modifications, according to this modification, the liquid passages in the nozzle 201j for supplying the sample liquid can be changed to vary the sample discharge ports 211 at the end of the nozzle 201j. By virtue of the operation, this modification also can attain meritorious results which are similar to those achieved by the modification shown in FIGS. 32 to 34.

Figure 36:
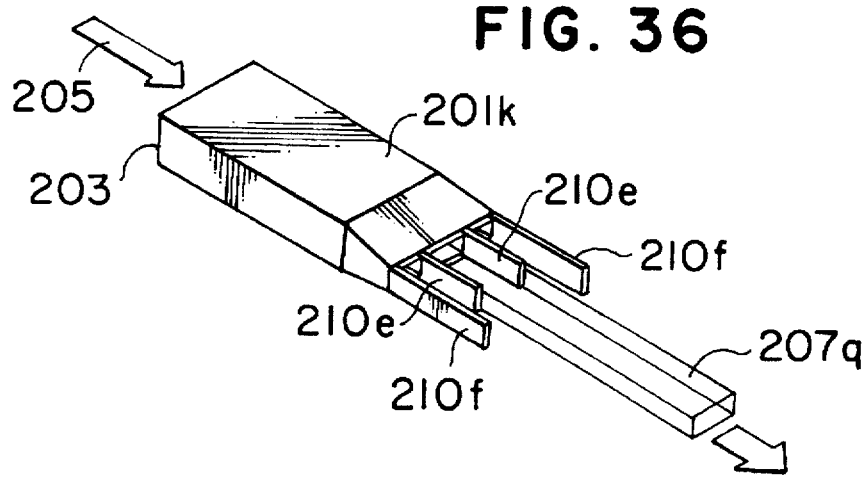
FIGS. 36 and 37 are perspective views of a nozzle according to still another modification, which show flows of different shapes in the flow cell, respectively.
Figure 37:
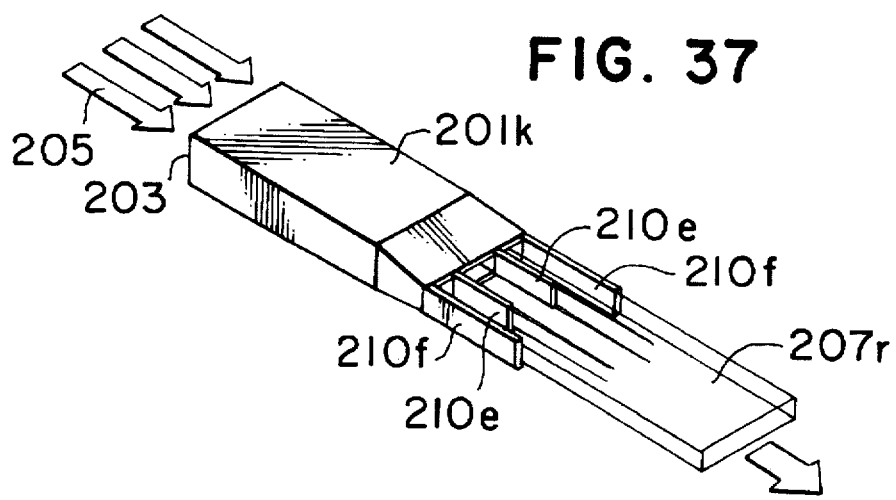

In a modification shown in FIG. 36 and 37, a nozzle 201k comprises three liquid passages each having a rectangular cross section. These liquid passages are arranged adjacent to one another side by side. A pair of plate-like guide 210e are provided on both sides of an outlet port of the central liquid passage, respectively. Further, another pair of plate-like guides 210f, which are longer than the guides 210e, are provided on both sides of the nozzle 201k, respectively. As shown in FIG. 36, when a sample fluid 205 is supplied to only the central nozzle liquid passage and discharged from the central outlet port at the end of the nozzle 201j at a predetermined flow rate, it forms a sample flow 207q in a sheath flow to flow through the flow cell passage at a predetermined flow velocity. At this time, the sample flow 207q is in a columnar shape in cross section, which is like the shape of the outlet port at the end of the nozzle 201k from which the sample liquid is being discharged. Further, since the sample flow 207q flows along the guides 210f with the opposite sides of the sample flow 207q guided by the guides 210f, it can scarcely suffer from turbulence at a junction of the nozzle end where the sample flow and the sheath flow join together, and a stable sample flow can be formed.

When the shape of the sample flow is changed, the sample liquid is supplied to all the nozzle liquid passages as shown in FIG. 37 and discharged from the three liquid passages at the end of the nozzle 201k. Thus, the sample liquid in the flow passages of the flow cell can be changed in shape from a sample flow 207q shown in FIG. 36 to a sample flow 207r shown in FIG. 37. By changing the shape of the sample flow as described above, meritorious results similar to those attained by the foregoing modifications can be obtained. That is, the width and the thickness of the sample flow can be changed by switching the plural liquid passages of the nozzle for discharging the sample. When the flow rate of the sheath liquid and that of the sample liquid are changed with the ratio of them kept constant, only the flow velocity can be controlled without changing the shape of the sample flow.

As described above, according to the flow cell apparatus of the invention, it is possible to form the sample flow of a constant width in the measuring portion, which is stable even at a high speed, to efficiently measure the sample liquid with high accuracy. Further, with the provision of the flow contraction passage portion, the flow can be further stabilized in this passage portion, and a flat sample flow of a cross section having a large aspect ratio can be formed. Therefore, when particles in the sample liquid are photographed by a CCD camera connected to a microscope, pictures of them can be taken within the range of a photographing visual field while being correctly focused on. As a result, the accuracy in photographing can be improved.

Further, as the flow can be stabilized in the accelerating passage portion, a sample flow at a high speed more than 1000 mm/second can be formed.

The sample flow in the flow cell apparatus flows stably while preventing the change and irregularity in the directions of the thickness and the width. Therefore, a sample flow having a uniform flow rate distribution in the widthwise direction can be realized.

In addition, since the sample liquid can continuously be supplied to the flow cell apparatus serving as the measuring portion in a short time, many kinds of samples can successively be measured.

As the sample liquid is not introduced into the measuring portion through a tube or the like but it can directly be supplied to a position adjacent to the measuring portion, the time required to form a sheath flow in the flow cell apparatus can significantly be shortened.

Since the flow passage through which the sample liquid passes is very short, the cleaning area can considerably be reduced and the time required to complete cleaning can also be shortened.

Additionally, as the sample flow in the flow cell can be set to have an optimum width for the imaging portion by adjusting the distance between guides, the width, the thickness and the flow velocity of the sample liquid can be switched when the photographing magnification is changed.

The flow cell apparatus of the invention can precisely perform image analysis, since the overall quantity of the sample liquid passes through the imaging region and a partially photographing of the particles at ends of the imaging region is prevented. Further, the volume of the sample liquid passing through the imaging region can accurately be known.

Moreover, sample flows having widths, thicknesses and flow rates suitable to plural types of examination conditions can successively be formed in the same flow cell. Therefore, examination can be performed precisely, the liquid passage system and the examination optical system can be simplified, the quantity of the sample required to performance examination can be reduced, and the time required to complete the examination can be shortened.

In addition, samples of plural types having widths, thicknesses and flow rates that suit the characteristics of the samples can successively be formed in the same flow cell. Therefore, an examination can be performed under the most suitable conditions for the examination optical system. Accordingly, the examination can precisely be performed.

What is claimed is:

1. A flow cell apparatus, comprising;
    sample liquid supply means for supplying a sample liquid to be measured;
    sheath liquid supply means for supplying a sheath liquid;
    flow cell means for defining a flow passage, said flow cell means having a transparent measuring portion providing an unobstructed view of said flow passage in at least one transversal direction thereof, said flow passage having a substantially constant width in a direction perpendicular to said direction of the unobstructed view;
    nozzle means provided in fluid communication with said sample liquid supply means for causing the sample liquid to flow into said flow passage of said flow cell means, said nozzle means having at least one discharge port disposed in said flow passage in a spaced relation from an inner wall thereof; said sheath liquid supply means being in fluid communication with said flow passage of said flow cell means at a position upstream of said at least one discharge port of said nozzle means with respect to a flow of the sample liquid to cause the sheath liquid to flow around said at least one discharge port and surround the sample liquid flow from said at least one discharge port to form a sheath flow; and
    guides provided at said at least one discharge port for regulating a width of the sample liquid flow in at least the direction perpendicular to said direction of the unobstructed view in said measuring port, wherein said guides are arranged so as to provide the sample liquid flow in said flow passage with a constant width at least at a portion of said flow passage at which said transparent measuring portion is provided.

2. The apparatus according to claim 1, wherein said guides are disposed on opposite sides of said at least one discharge port in a widthwise direction of said flow passage for guiding the sample liquid from said at least one discharge port to form a stable flow of the constant width.

3. The apparatus according to claim 1, wherein said sample liquid supply means is disposed separately from said flow cell means and is formed to be selectively connected to said flow cell means in a sealed manner.

4. The apparatus according to claim 1, wherein said sample liquid supply means and said sheath liquid supply means are capable of changing a quantity of said sample liquid and that of said sheath liquid supplied to said flow cell means, respectively.

5. The apparatus according to claim 1, wherein said sheath liquid supply means is provided with a waste liquid port for discharging a liquid for cleaning said flow passage in said flow cell means.

6. The apparatus according to claim 1 further comprising holder means for holding said flow cell means, wherein said flow cell means is attached to said holder means at both ends of said flow passage, said sheath liquid supply means includes an annular sheath liquid supply portion which is sealingly connected to one of said ends of said flow passage and mounted on said holder means, and said nozzle means is inserted into said flow passage of said flow cell means through said sheath liquid supply portion.

7. The apparatus according to claim 1 further comprising means for varying any one of a flow rate of the sample liquid, a flow rate of the sheath liquid and a shape of said discharge port of said nozzle means to change a velocity of the sample liquid flow and a cross sectional shape thereof.

8. The apparatus according to claim 1 further comprising means for varying at least one of a flow rate of the sample liquid, a flow rate of the sheath liquid and a shape of said at least one discharge port of said nozzle means to independently change a velocity, the width and a height in the unobstructed view direction of the sample liquid flow.

9. The apparatus according to claim 1, wherein said flow cell means further includes means provided upstream said measuring portion for narrowing the sheath flow in the unobstructed view direction of said measuring portion to increase a velocity of the sample liquid flow in the sheath flow and reduce a thickness of the sample liquid in the unobstructed view direction to form a flat flow.

10. The apparatus according to claim 9, wherein said sheath flow narrowing means is set to increase the velocity of the sample liquid flow to 1000 mm/second or higher.

11. The apparatus according to claim 9, wherein said sheath flow narrowing means constructed to reduce the thickness of the sample liquid for photographing particles of the sample liquid through a microscope in said measuring portion.

12. The apparatus according to claim 9, wherein said sheath flow narrowing means comprises a portion of said flow passage having a height in the unobstructed view direction, which height is gradually decreased downstream.

13. The apparatus according to claim 9, wherein said nozzle means further includes means for changing the width of the sample liquid flow.

14. The apparatus according to claim 9, wherein said guides are disposed on opposite sides of said at least one discharge port in a widthwise direction of said flow passage for guiding the sample liquid from said at least one discharge port to form a stable flow of the constant width.

15. The apparatus according to claim 1, wherein said nozzle means further includes means for changing the width of the sample liquid flow in accordance with a measuring range in said measuring portion.

16. The apparatus according to claim 15, wherein said flow width changing means comprises a plurality of discharge ports of said nozzle means, which are individually and selectively communicated with said sample liquid supply means.

17. The apparatus according to claim 15, wherein said flow width changing means includes at least one discharge port of said nozzle means, which at least one discharge port is formed to be variable in opening width.

18. The apparatus according to claim 15, wherein said guides comprise fixed guide plates which are respectively provided on both sides of said at least one discharge port in a widthwise direction of said flow passage, and wherein said means for changing the width of the sample liquid flow includes means for changing a flow rate of the sample liquid flow and said fixed guide plates each of said guides being formed to enable the sample liquid to flow over said fixed guide plates when said sample liquid is provided at greater than a predetermined flow rate.

19. The apparatus according to claim 15, wherein said flow width changing means comprises said guides which are movable guide plates provided on both sides of said at least one discharge port in a widthwise direction of said flow passage, respectively.

20. The apparatus according to claim 1, wherein said nozzle means further includes means for changing a shape of the sample liquid flow.

21. The apparatus according to claim 20, wherein said flow shape changing means includes said at least one discharge port of said nozzle means, which at least one discharge port is variable in opening shape.

22. The apparatus according to claim 20, wherein said flow shape changing means includes the nozzle means which nozzle means mounted for rotation about a longitudinal axis thereof in said flow passage.

23. The apparatus according to claim 20, wherein said flow shape changing means comprises a plurality of discharge ports of said nozzle means, which are arranged both in a widthwise direction of said flow passage and in the unobstructed view direction of said measuring portion and are individually and selectively communicated with said sample liquid supply means.

24. The apparatus according to claim 20, wherein said flow shape changing means are a plurality of discharge ports of said nozzle means, which each have different shapes of openings and are individually and selectively communicated with said sample liquid supply means.

25. The apparatus according to claim 1, wherein said nozzle means is detachably fastened to said flow cell means.

26. The apparatus according to claim 25, wherein said nozzle means is sealingly mounted to said flow cell means with said at least one discharge port of said nozzle means inserted into said flow passage.

27. The apparatus according to claim 1, wherein said flow passage of said flow cell means has a substantially rectangular cross section, a height of which in the unobstructed view direction of said measuring portion is smaller than the width of said flow passage.

28. The apparatus according to claim 27, wherein said guides comprise a pair of elongated, stationary guide plates respectively provided on both sides of said at least one discharge port in the widthwise direction of said flow passage, and said guide plates are inclined inwardly toward each other in a manner that the sample liquid smaller than a certain flow rate is regulated into a fixed width and the sample liquid more than the certain flow rate flows over said guide plates to form a wider flow.

29. The apparatus according to claim 27, wherein said at least one discharge port of said nozzle means is defined by a central portion and two side portions which are movable with respect to said central portion to change a width of opening of said at least one discharge port, and said nozzle means further includes actuator means for moving said two side portions.

30. The apparatus according to claim 27, wherein said nozzle means includes an elastic tube of a circular cross section connected to said sample liquid supply means, a pair of pressing plates movably provided adjacent to said elastic tube to change the cross section of said elastic tube, and actuator means for moving said pressing plates.

31. The apparatus according to claim 27, wherein guides comprise a pair of elongated guide plates respectively provided for pivoting movement on both sides of said at least one discharge port in the widthwise direction of said flow passage to change a distance between ends of said guide plates to regulate the width of the sample liquid flow, and wherein actuator means for driving said guide plates are further provided.

32. The apparatus according to claim 27, wherein said at least one discharge port of said nozzle means has a substantially rectangular cross section, said nozzle means is mounted in said flow passage for rotation around a longitudinal axis of said nozzle means, and said nozzle means further includes actuator means for rotating said nozzle means and wherein said guides comprise a pair of stationary guide plates respectively provide on shorter side portions of said at least one discharge port.

33. The apparatus according to claim 27, wherein said nozzle means includes a first nozzle having a substantially rectangular cross section and a second nozzle disposed in said first nozzle said first and second nozzles including first and second discharge ports, respectively, and wherein said guides comprise a pair of stationary guide plates respectively provided on both sides of said discharge port in the widthwise direction of said flow passage, said second nozzle having a substantially rectangular cross section which is smaller than that of said first nozzle, and said second nozzle being provided, respectively on both sides said second discharge port thereof in the widthwise direction of said flow passage, with a pair of stationary guide plates which are smaller in size than said guide plates of said first nozzle, and wherein said first nozzle selectively communicates with said sample liquid supply means to change a shape of the sample liquid flow passing through said measuring portion.

34. The apparatus according to claim 33, wherein said second nozzle is movably mounted to protrude from said first nozzle into said flow passage along a longitudinal axis of said first nozzle, and said nozzle means further includes actuator means for moving said second nozzle.

35. The apparatus according to claim 27, wherein said nozzle means has three discharge ports arranged in the widthwise direction of said flow passage, and the two discharge ports at opposite sides of said three discharge ports selectively communicate with said sample liquid supply means to change the width of the sample liquid flow.

36. The apparatus according to claim 35, wherein said guides comprise a first pair of elongated guide plates respectively provided on both sides of said nozzle means in the widthwise direction of said flow passage to extent substantially in parallel to the direction of the sample liquid flow, and a second pair of elongated guide plates respectively provided on both sides of a central discharge port of said three discharge ports in the widthwise direction of said flow passage, said second pair of elongated guide plates extending substantially in parallel to the direction of the sample liquid flow, and said first guide plates being larger in length in the direction of the sample liquid flow than said second guide plates.

37. The apparatus according to claim 27, wherein said nozzle means includes a plurality of discharge ports disposed around a common longitudinal axis, and said plurality of discharge ports selectively communicate with said sample liquid supply means to vary a combination of said discharge ports for discharging the sample liquid to change a shape of the sample liquid flow passing through said measuring portion.

38. The apparatus according to claim 37, wherein said discharge ports each have a substantially square cross section and are arranged adjacent to one another to collectively define a larger square.

39. The apparatus according to claim 37, wherein said nozzle means includes a central discharge port disposed on said common longitudinal axis, the other discharge ports are situated around said central discharge port at equal intervals, and said central discharge port and said other discharge ports each have an identical circular cross section.

40. The apparatus according to claim 27, wherein said flow passage of said flow cell means includes a parallel flow passage portion which passes through said measuring portion and has a height substantially constant in the unobstructed view direction, and a flow contraction passage portion which is disposed upstream said parallel flow passage portion and has a height gradually decreased toward said parallel flow passage portion.

41. The apparatus according to claim 40, wherein the height of said parallel flow passage portion is set in accordance with a depth of focus of a microscope to be used in measurement.

42. The apparatus according to claim 40, wherein said discharge port of said nozzle means has a substantially square cross section, and said guides comprise a pair of elongated guide plates respectively provided on both sides of said discharge port in a widthwise direction of said flow passage to extend substantially in parallel to a direction of the sample liquid flow.

43. The apparatus according to claim 40, wherein said discharge port of said at least one nozzle means has a substantially flat, elongated cross section, a height of which in the unobstructed view direction of said measuring portion is smaller than the width of said flow passage.

44. The apparatus according to claim 40, wherein said flow passage of said flow cell means is further provided with a deceleration flow passage portion, which is disposed downstream said parallel passage portion and increased in height gradually from said parallel flow passage portion.

45. The apparatus according to claim 44, wherein said flow passage of said flow cell means is further provided with another parallel flow passage portion which has a substantially constant height and is disposed upstream said flow contraction passage portion.

46. The apparatus according to claim 40, wherein said flow passage of said flow cell means is defined by plate-like members joined together, said flow contraction passage portion is defined by a pair of flow contracting plates, and said flow contracting plates each have a trapezoidal cross sectional shape in a direction of the sample liquid flow and are secured in said flow passage to face each other.

47. The apparatus according to claim 46, wherein said plate-like members are transparent.

48. The apparatus according to claim 40, wherein said nozzle means has three discharge ports arranged in a widthwise direction of said flow passage, the two discharge ports at opposite sides of said three discharge ports being selectively communicated with said sample liquid supply means to change the width of the sample liquid flow.

49. The apparatus according to claim 48, wherein said guides comprise first and second pairs of elongated guide plates, said two discharge ports being provided at their outermost sides in the widthwise direction of said flow passages with said first pair of elongated guide plates, respectively, which each extend substantially in parallel to the sample liquid flow, a central one of said three discharge ports being provided at both sides thereof in the widthwise direction of said flow passage with said second pair of elongated guide plates, respectively, which each extend substantially in parallel to the sample liquid flow, and wherein each of said first pair of elongated guide plates is larger in length in the direction of the sample liquid flow than each of said second pair of elongated guide plates.

50. The apparatus according to claim 40, wherein guides comprise a first pair and a second pair of elongated guide plates respectively provided on both sides of said at least one discharge port in the widthwise direction of said flow passage, said second pair of elongated guide plates being smaller in length in the direction of the sample liquid flow than said first pair of elongated guide plates and inclined inwardly toward each other to form the sample liquid flow of a small width, and said first guide plates being disposed outside the respective second guide plates and extending substantially in parallel to the direction of the sample liquid flow to form the sample liquid flowing over the second pair of elongated guide plates into a flow of a constant width.

51. The apparatus according to claim 50, wherein each of said second pair of elongated guide plates is tapered in a downstream direction.

* * * * *